(12) United States Patent
Boysworth

(10) Patent No.: US 7,127,372 B2
(45) Date of Patent: Oct. 24, 2006

(54) RETRO-REGRESSION RESIDUAL REMEDIATION FOR SPECTRAL/SIGNAL IDENTIFICATION

(75) Inventor: Marc Kenneth Boysworth, Alexandria, VA (US)

(73) Assignee: ITT Manufacturing Enterprises, Inc., Wilmington, DE (US)

( * ) Notice: Subject to any disclaimer, the term of this patent is extended or adjusted under 35 U.S.C. 154(b) by 0 days.

(21) Appl. No.: 11/064,290

(22) Filed: Feb. 24, 2005

(65) Prior Publication Data

US 2006/0190216 A1    Aug. 24, 2006

(51) Int. Cl.
G01N 31/00    (2006.01)

(52) U.S. Cl. .......................... 702/179; 702/22; 702/27; 702/30

(58) Field of Classification Search ................ 702/179, 702/19, 22, 23, 25, 27, 30–32, 21
See application file for complete search history.

(56) References Cited

U.S. PATENT DOCUMENTS

| | | | | |
|---|---|---|---|---|
| 5,379,238 A | * | 1/1995 | Stark ........................... | 703/11 |
| 5,446,681 A | * | 8/1995 | Gethner et al. ............... | 702/27 |
| 5,568,400 A | * | 10/1996 | Stark et al. .................... | 702/85 |
| 5,572,125 A | * | 11/1996 | Dunkel ........................ | 324/307 |
| 6,137,104 A | * | 10/2000 | Webb et al. ................. | 250/226 |
| 6,172,744 B1 | * | 1/2001 | Scharlack et al. ............ | 356/39 |
| 2005/0110503 A1 | * | 5/2005 | Koehler et al. ............. | 324/710 |

OTHER PUBLICATIONS

Freckleton, R.P.; "On the Misuse of Residuals in Ecology: Regression of Residuals vs. Multiple Regression"; Journal of Animal Ecology, 2002, vol. 71, pp. 542-545, no month.
Marten, H. et al.; "Multivariate Calibration"; John Wiley & Sons, NY, 1989; pp. 199-213, no month.

* cited by examiner

Primary Examiner—Hal D. Wachsman
(74) Attorney, Agent, or Firm—Edell, Shapiro & Finnnan, LLC

(57) ABSTRACT

An improved regression-based qualitative analysis algorithm useful when the mixture to be analyzed contains a compound not in the library spectra, a so-called unknown. A regression of a measured spectrum is computed against the library spectra. This regression is referred to as a "master" regression. Estimated mixing coefficients for an estimated spectrum are computed from the regression. Next, a residual error is computed between the estimated spectrum and the measured spectrum. Peaks in the residual error are identified that extend in a direction opposite to that of peaks in the measured spectrum. These peaks are referred to as "negative" peaks. A regression is performed on the peaks. This is referred to as a "retro-regression" to be distinguished from the master regression performed on the measured spectrum. Using information from the retro-regression, corrected mixing coefficients are computed and the process repeats.

17 Claims, 23 Drawing Sheets

Chemicals in the Library

| | | |
|---|---|---|
| 2clbutane | 2clpropane | cn |
| cr | cs | cx |
| dem | ep | ga |
| gb | gd | gf |
| hd | hn | hq |
| ht | m xylene | mdea |
| mes | mp | xylene |
| p xylene | acetone | acetonitrile |
| acrolein | acrylonitrile | benzene |
| chloroethylether | chloropicrin | cyclohexane |
| dibenzosuberone | dichloroethene | ethanol |
| ethylene | formalehyde | hexane |
| hydrazine l | spropanol | methanol |
| nicotine | pentane | tetrafluoroethene |
| thf | toluene | |

FIG. 4

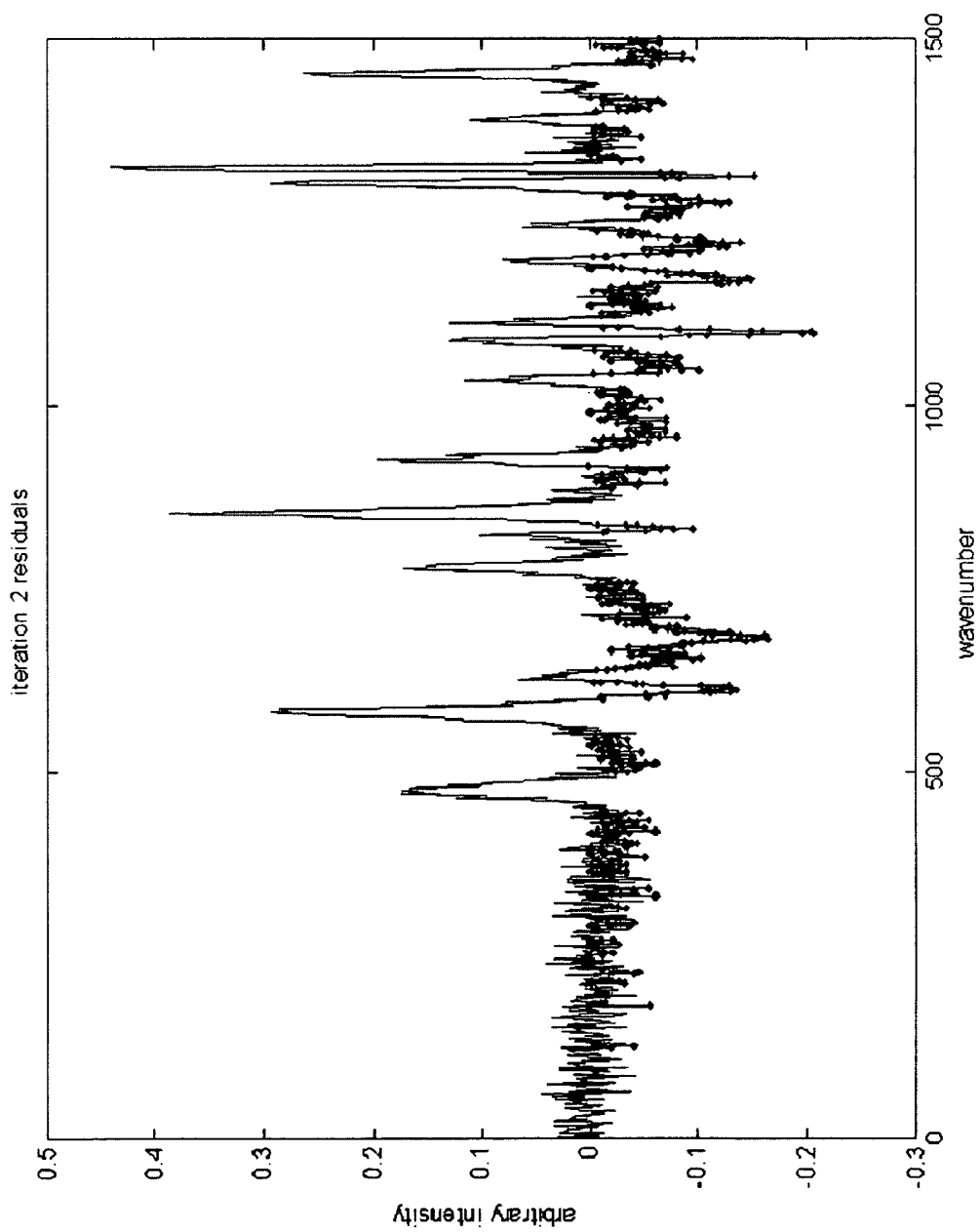

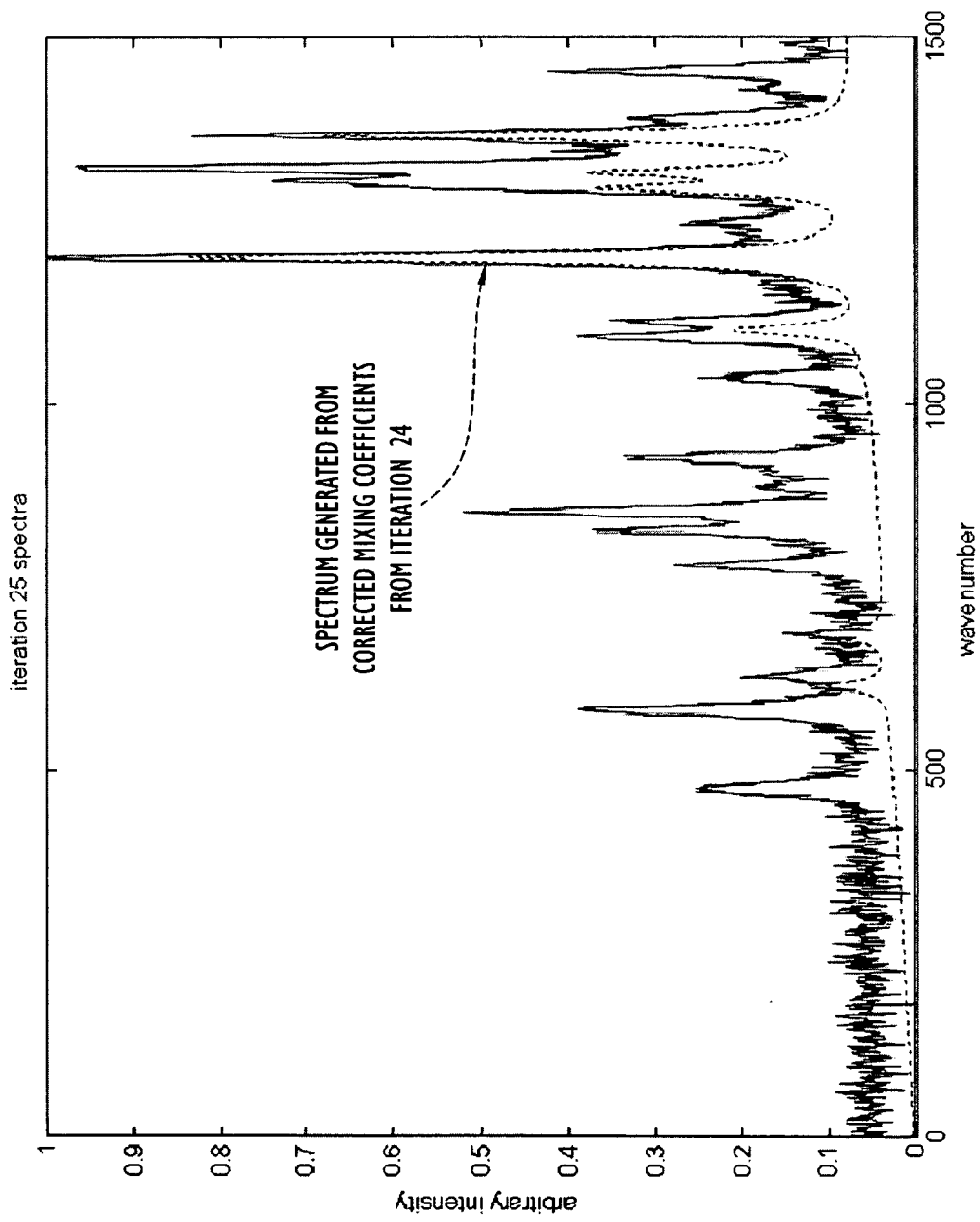

RETRO-REGRESSION RESIDUAL REMEDIATION FOR SPECTRAL/SIGNAL IDENTIFICATION

BACKGROUND OF THE INVENTION

The present invention is directed to a method for improving performance of spectroscopic algorithms that are used to classify spectra, and more particularly to techniques to make spectroscopic algorithms more robust when analyzing data from unknown constituents.

Spectroscopy is a key technology for remote detection of biological or chemical constituents (such as biological and chemical warfare agents). The common thread in all spectroscopies is that each chemical and/or biological substance has a unique spectrum due to their unique structure. One of the goals of qualitative spectroscopy is to determine the component makeup of a substance given a library of the spectra of pure compounds. Quantitative analysis is not always necessary, and based on the sensor's construction and its operation, may not be possible. The use of spectroscopy requires algorithms that are capable of classification and de-convolution of spectra that arise from mixed substances. Regression methods are commonly used for qualitative data analysis. Multiple Linear Regression (MLR) methods are extremely useful for classification and de-convolution of mixed signals with a set of known library signals, called library spectra. Operationally, a library of spectra and a measured spectrum are input into the MLR model. The output is a vector called "mixing coefficients" that describes the quantities of the library spectra needed to linearly add the library spectra thereby generating a "best-fit" spectrum that is sufficiently close to the measured spectrum. Calculation of the mixing coefficients varies by model, and constraints may be employed. The advantages of MLR models for mixed signal identification include simplicity of implementation and operation, simultaneous determination of multiple compounds, speed of operation and the ability to use "pure" library spectrum (rather than a population of spectra to span the error space). In addition, most MLR models are based on rules that are consistent with the physics of spectroscopy in general. One particular advantage of many simple MLR models, including Classical Least Squares (CLS), is that no assumptions about the underlying probability densities of the signals need to be made or determined a priori. The importance of the contemporary algorithms cannot be overstated as these techniques are at the forefront of unmanned chemical and biological warfare detection.

These contemporary algorithms perform well against known compounds that are represented in the spectral library but are limited in their ability to handle unknown constituents that are not present in the library. Typically such unknowns will cause false alarms, as the algorithms attempt to use the library to describe the spectral features introduced by the unknowns. Historically, unknown spectral constituents are the Achilles heel of spectroscopic analysis. When performing spectroscopy in an uncontrolled setting (e.g., remote spectroscopic sensing of the environment) the assumption that the library contains everything that might generate a spectroscopic response is violated. At the onset, this puts conventional algorithms at a disadvantage, due to their inability to compensate for unknowns. Furthermore, many unknowns may share spectral similarity with any number of chemicals in the library, which further exacerbates the false alarm problem. For example, the functional group phosphate is responsible for a characteristic Raman peak in many chemical warfare agents such as Sarin, Soman, and Tabun. Similar chemical structure and therefore similar spectral features may be found in many of the pesticides sold in retail gardening stores. Unknown signals are ubiquitous and frequently degrade the sensor's performance even on well characterized signals. Thus, when unknowns are present, they tend to cause false positive detections. This introduces type II errors (accepting a false hypothesis).

Due to the almost infinite number of substances that may be encountered, it is impossible to include every possible constituent in the library spectra. This leaves the qualitative spectroscopist with three choices:

1. Ignore the unknowns and hope that they do not affect the analysis.
2. Control the sample rigorously—this may mean that samples are pre-treated to separate out anything besides the items of interest.
3. Build algorithms and routines that are robust against unknowns.

The first choice is the most common solution: make the a priori assumption that unknowns will not be present or if they are present, they will not cause significant problems. Although this greatly simplifies the problem of identification, for real world applications, those are dangerous assumptions to make. For these reasons, the second choice is often used in industrial settings, laboratory settings, and in environmental testing, where it is convenient to obtain a sample and perform the wet chemistry or preparative separation on it prior to (and sometimes in conjunction with) spectroscopic analysis. Pre-treatment is not always the most desirable choice, especially if the samples being analyzed are dangerous or if the samples are being sensed at such a distance, frequency, or under other circumstances that make pre-treating impossible. Thus, the better solution for performing real-time or in-the field measurements of un-treated samples is to make algorithms and routines robust to unknowns.

Attempts have been made to overcome these problems by either adding the unknown features into a calibration library, or subtracting them from the sample. All of these techniques involve analysis of quantitative data, and seek to correct both for unknowns and for disturbances in the spectrum due to disparate environmental effects. These methods require extensive knowledge of the system being measured, which is not available when performing remote analysis of environmental samples, in which the sensor may contain some variance, and the samples analyzed are unconstrained with respect to chemical composition. Another disadvantage for these competing attempts is that they require expert knowledge, and frequently expert operation, which hinders the ability of the algorithm to work unassisted, as a remote, real-time system would need to.

What is needed is a technique for automatically correcting spectroscopic analysis for unknown components present in the measured mixture.

SUMMARY OF THE INVENTION

Briefly, a system and method are provided for improving regression-based qualitative analysis when the mixture to be analyzed contains a compound not in the library spectra, a so-called unknown. A regression of a measured spectrum taken of a sample is computed against the library spectra. This regression is referred to as a "master" regression. Estimated mixing coefficients of the sample are computed from the regression. Next, a vector of residual error is computed using the "best-fit" spectrum (generated using the library and the estimated mixing coefficients) and the measured spectrum. Peaks in the residual error are identified that extend in a direction opposite to that of peaks in the measured spectrum. These peaks are referred to as "negative" peaks. A regression is performed on the "negative" peaks with the library. This is referred to as a "retro-regression," to be distinguished from the master regression performed on the measured spectrum. The mixing coefficients generated in the retro-regression are used to compensate for overprediction in previous steps. Using the retro-regression mixing coefficients, corrected mixing coefficients are computed. This process repeats where the corrected mixing coefficients replace the estimated mixing coefficients for a new estimated spectrum that is used to compute a new residual error.

Furthermore, the corrected mixing coefficients may be examined to determine whether there is a member of the library whose mixing coefficient is less than a threshold. If so, that member is removed from the library spectra and a new master regression is computed without that library member. The new estimated mixing coefficients are used for computing the residual error at the next iteration.

Termination of the process may occur when there are no more negative peaks in the residuals, there are no more members in the library spectra, or a maximum number of iterations are reached.

This retro-regression remediation technique makes MLR algorithms more robust to unknowns. Used in conjunction with MLR techniques, estimates are generated in a manner that utilizes the error structure which arises from the constraints of spectroscopy to eliminate false alarms. Furthermore, this approach allows for improved analysis of the unknown constituents. The known compounds may be identified, and removed, storing the best-unknown spectrum for further "forensic" chemical analysis on it at a later date. No knowledge is assumed about the composition of the sample. This algorithm works with minimum user input. It is as an add-on to other regression techniques (i.e. Classical Least Squares) to eliminate false positive errors. However, the techniques described herein may be generalized to improve performance of any other regression model that follows the basic assumptions of optical spectroscopy.

The above and other objects and advantages will be more readily apparent when reference is made to the following description taken in conjunction with the accompanying drawings.

BRIEF DESCRIPTION OF THE DRAWINGS

FIG. 4 lists the members of the library spectra for an example described herein.

FIG. 7B is a plot showing the residual error between the measured spectrum and the estimated spectrum shown in FIG. 7A for iteration 2.

FIG. 8A is a plot showing the measured spectrum and an estimated spectrum at iteration 25 that is generated from the corrected mixing coefficients from iteration 24.

DETAILED DESCRIPTION

Figure 1:
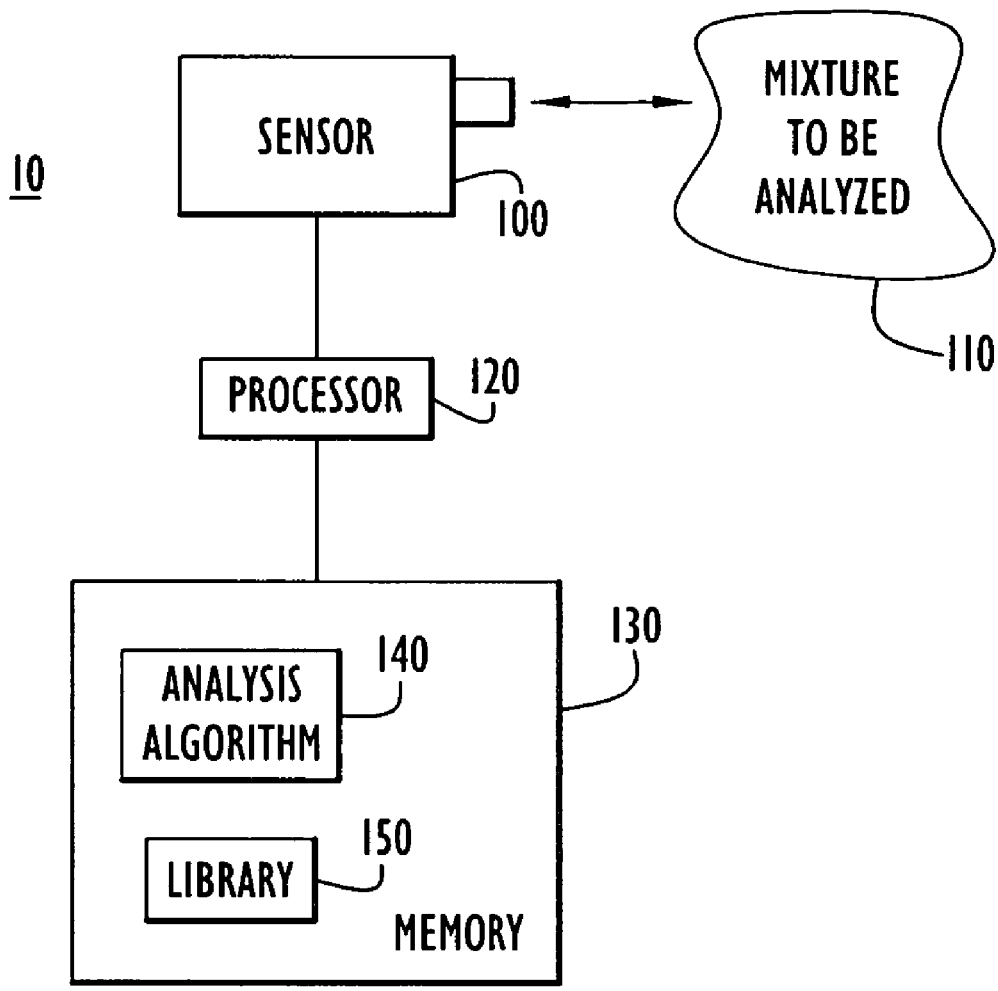
FIG. 1 is a block diagram of a spectroscopic analysis system.

Referring first to FIG. 1, a spectroscopic analysis system 10 is shown comprising a sensor 100 coupled to a processor 120. Memory 130 is provided that stores the software that performs the analysis algorithm 140 and a library 150 that contains spectrum data associated with numerous chemicals against which the analysis algorithm 140 operates. The sensor 100 scans or otherwise performs a spectroscopic measurement on a mixture 110 to be analyzed. The mixture 110 may be a solid, liquid or gas substance.

Figure 2:
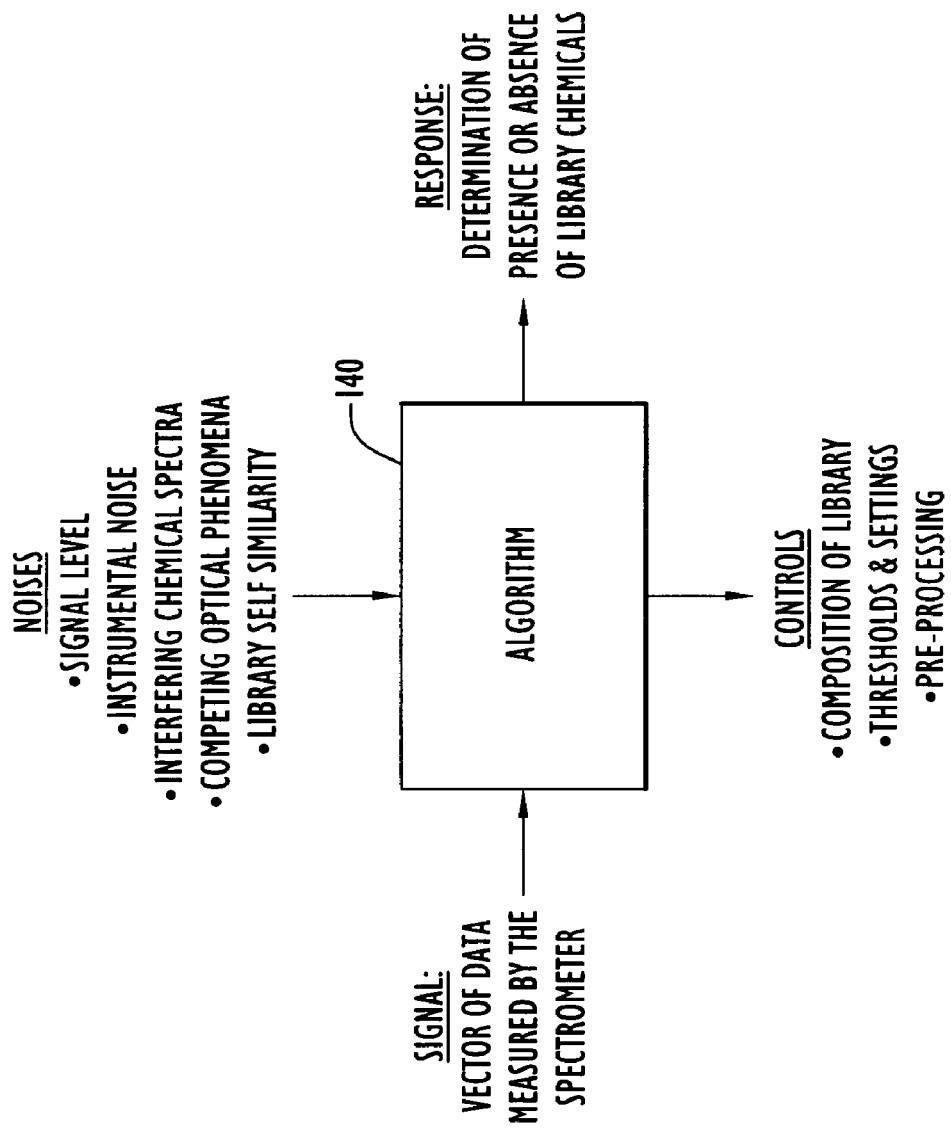
FIG. 2 is general flow chart of a spectroscopic analysis process.

As shown in FIG. 2, the spectroscopic analysis process involves executing the analysis algorithm 100 on the measured spectrum data produced by the sensor against the library spectra. The outputs of the analysis algorithm are qualitative spectrum analysis results on the mixture.

Certain assumptions are made when utilizing current spectroscopic analysis algorithms, and when these assumptions are met everything works well and the algorithm provides reliable results. The assumptions include linearity, linear additivity, all pure spectra known, uniqueness, and non-negativity of physical quantities. However, when performing remote sensing, the all pure spectra known assumption is frequently violated, causing problems with how these algorithms handle unknowns. The typical result is an overestimation of "library" chemicals, often resulting in false positive alarms (Type II errors).

Assumptions may be made regarding error structures arising from regression-based techniques applied to spectroscopic data. Since a substance may either be present in a certain quantity, or is absent, concentration quantities have a minimum of zero. Unlike with time based signals such as radar, there is no signal-based interference such as phase mixing. For this reason, in conventional spectroscopy spectra may always add together, but will never cancel each other out, and therefore are never assigned negative concentration/intensity values in the absence of specific data pre-processing techniques not employed herein. Using these assumptions, the algorithm described herein functions as an add-on to other regression techniques that would eliminate false positive errors. If the residual error is defined as the modeled signal subtracted from the original signal (spectrum) and the signal is one that extends in the positive direction, then errors that extend in the positive direction are portions of the original spectrum that are poorly modeled (i.e., an unknown spectrum or portions thereof) and errors in the negative direction are indicators that library spectra members are being erroneously used to model an unknown. Identification of the spectra causing the negative residuals, and removal of those spectra from the library will eliminate the major source of false positives in regression based classification models. This algorithm is referred to as a retro-regression residual removal ("R4") algorithm.

The R4 algorithm may be an add-on to Multiple Linear Regression (MLR) type regression models that follow the basic assumptions of optical spectroscopy. It has the following benefits:

1. Eliminates of false alarms,
2. Operates in the presence of unknown constituents,
3. Improves quantitative accuracy (when desired), Theory of R4

When using Classical Least Squares (CLS) for multiple component identification or quantification, the inherent assumptions made are:

Linearity: The relationship between the intensity of the signal vector and its concentration (i.e. quantity) is linear over the range measured.

Linear additivity: The signal response to a mixture is the same as if the signals were collected separately and added together subsequent to collection.

All pure spectra known: The constituents of the mixture are all present in the library of signals.

Uniqueness/Non-Singularity: The library signals all have some degree of uniqueness, even if there are certain similar features between signals in the library, and none of the signals may be added such that the result is collinear with any other signal.

Non-Negativity: Although not a mathematical requirement, frequently the concentration or quantity values are constrained to non-negative estimates because negative values have no physical meaning when quantities of material are concerned.

The signals and quantities of interest include:
r=unknown signal;
S=library of pure signals; and
c=concentrations or relative amounts of each signal in S In the MLR model, if all of the assumptions hold, it may be stated that $$r = cS$$

and that S and r may be used to generate an estimate of c, $\hat{c}$, in the following manner $$rS^+ = \hat{c}$$

where $\hat{c}$ is an estimate of c, whose fidelity is based on the completeness and accuracy of S, any error in the system, the computation of the pseudo-inverse of S, $S^+$, and the compliance with the assumptions of MLR. The (unknown) signal of interest may be reconstructed using $\hat{c}$ and S.

$$\hat{r} = \hat{c}S$$

The fidelity of this reconstruction, $\hat{r}$, depends on the factors listed above. A vector of residual errors, $\epsilon$ may be generated by looking at the difference between r and $\hat{r}$.

$$\epsilon = r - \hat{r}$$

If all of the assumptions hold, the vector of residual errors $\epsilon$ should be the random noise in the system, and tends not to be intrinsically useful or interesting. However, if the assumptions are violated, the residual error vector $\epsilon$ contains information that is useful in determining the source of the violations.

If the errors are computed in the manner described above, the errors could be described as coming from three sources. The first source is the signal that arises from noise in the instrument. This tends to be random and uninteresting for the sake of this analysis. The second source is the spectrum of peaks that were in the measured spectrum that are not fit by the library members. Peaks in this direction are typically indicative of under-predicted peaks which are caused either by the presence of an unknown, or by under-prediction of known substances. The third source of error is due to over-prediction (and often mis-prediction) which occurs when library spectra are used to try to fit unknowns. The error caused by these peaks extends in the direction opposite to that of the original peaks in the measured spectrum.

Depending on the type of spectroscopy, peaks are portrayed in many ways. In emissive-type spectroscopy (Raman, Fluorescence, Mass Spectrometry) peaks extend upward from some baseline. In absorbance-type spectroscopy (Active NIR, UV-Vis absorbance) the peaks extend down from some baseline or theoretical absolute (e.g., 100% transmission). Both of these types of spectroscopy could be deemed monotonic, since when peaks are observed, the peaks extend in only one direction. This is contrasted with passive IR which has peaks that extend in both directions. Therefore, when negative residuals are mentioned, the intention is to describe peaks that extend in the direction opposite to the normal extension of the peaks.

Figure 3:
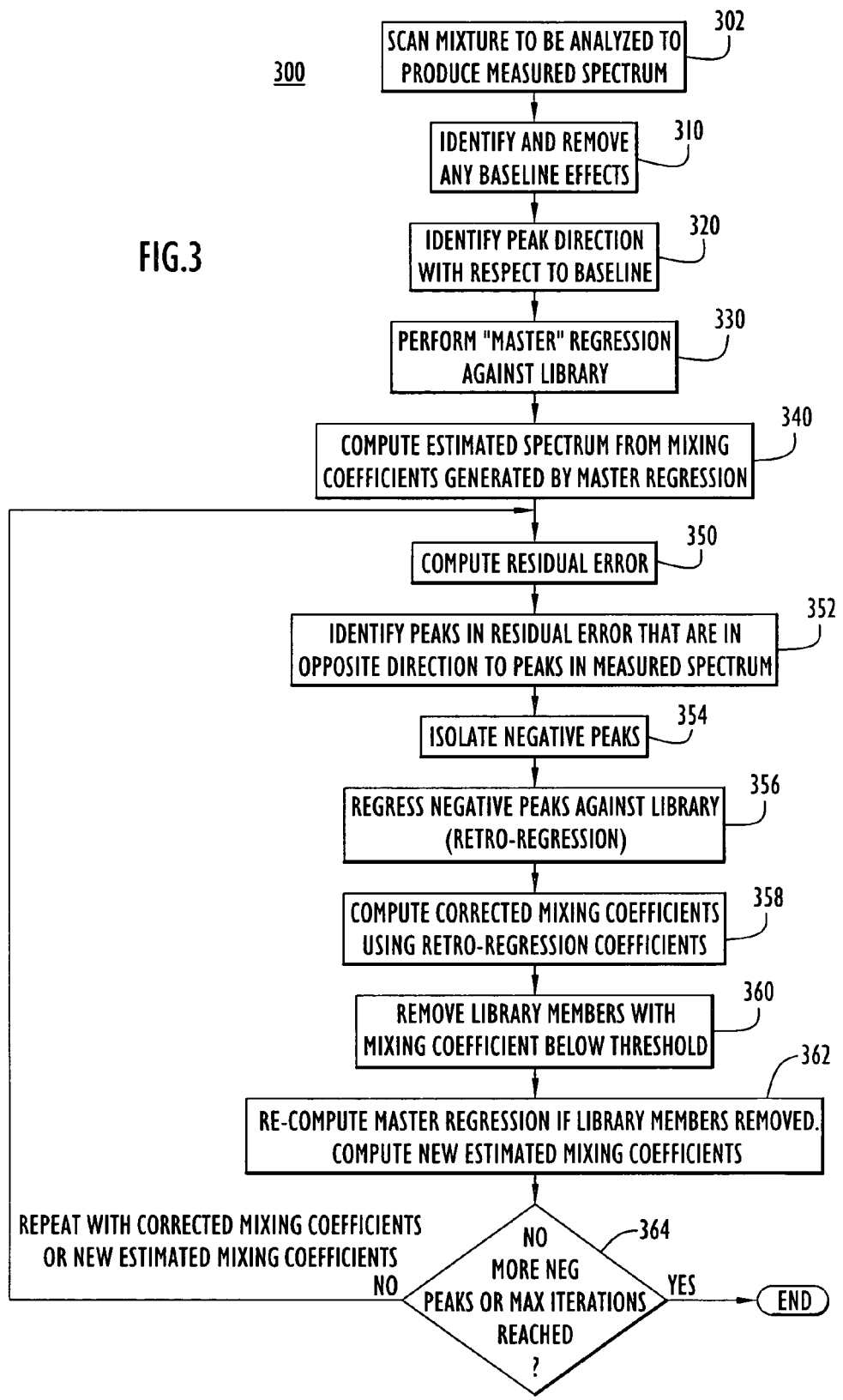
FIG. 3 is a flow chart depicting steps of the spectroscopic analysis process employing the retro-regression residual remediation algorithm.

Referring to FIG. 3, the R4 process 300 will be described. In step 302, a mixture to be analyzed is scanned or monitored in order to collect measured spectrum data. Next, in step 310, any baseline effects in the measured spectrum are identified and removed. Baseline effects, such as CCD dark current, fluorescence in the case of Raman Spectroscopy, or non-coherent scattering in the case of NIR spectroscopy are phenomena which will introduce some bias into the spectra. In order to determine the direction of the residuals relative to the original signal, this baseline must be identified. In step 320, the peak direction in the measured spectrum is identified with respect to the baseline. For example, it is determined whether the peaks in the measured spectrum are positive or negative with respect to the baseline. Next, in step 330, a "master" regression is performed on the measured spectrum against the library spectra. For example, an MLR regression may be used in step 330. In step 340, initial estimated (or best-fit) mixing coefficients are computed of the sample from the master regression. An estimated or "best-fit" spectrum is generated using the library and the estimated mixing coefficients.

A loop is defined by steps 350 through 364 during which corrected mixing coefficients are computed using a "retro-regression" computation. The corrected mixing coefficients produced at the completion of an iteration through the loop replace the estimated mixing coefficients computed in step 350 for purposes of computing a new residual error. Loop control step 364 tests whether certain criteria are met to stop iterating through the loop, and if none of these criteria is met, another iteration is made through the loop.

More specifically, in step 350, the residual error between the estimated spectrum and the measured spectrum is computed by subtracting the estimated spectrum from the measured spectrum. The residual error is also referred to herein as the "residuals". The first time into the loop (iteration 0), the estimated spectrum is the best-fit spectrum computed in step 340. In step 352, peaks are identified that extend in a direction opposite from the peaks in the measured spectrum. These peaks may be referred to as "negative" peaks, but it should be understood that they may extend in a positive direction if the peaks in the measured spectrum extend in a negative direction. Next, in step 354, the negative peaks are isolated. Then, in step 356, a "retro-regression" computation is performed. For example, the same regression method that was used to compute the master regression is used to compute the retro-regressions in order to remove specific deleterious effects that the master regression introduced. That is, the negative peaks are regressed against the library spectra to produce corrections to the originally over-predicted master mixing coefficients. In step 358, the retro-regression coefficients computed in step 356 are used to compute corrected mixing coefficients by subtracting the retro-regression mixing coefficients from the estimated mixing coefficients computed at the prior iteration, or if the first iteration, then the mixing coefficients generated from the master regression in step 340. This corrects the master regression concentration estimates computed during the first iteration.

Next, in step 360, any member in the library whose estimate in the corrected mixing coefficients is less than a threshold (typically the precision of the computer: $10^{-16}$) is removed. And in step 362, if a library member is removed in step 360, then the master regression (already once performed in step 330) is re-computed for the measured spectrum against the (new) library that now does not include the library member(s) removed in step 360. New (estimated) mixing coefficients are consequently computed in step 362 and used in the subsequent steps in place of the corrected mixing coefficients computed at the prior iteration for purposes of computing the residual error in step 350.

In the loop control step 364, a determination is made whether there are no more members of the library (as a result of the removal in step 360), no more negative peaks remain or a maximum number of iterations have been reached. If any of these criteria are met in step 364, the process 300 terminates and the estimated mixing coefficients computed up to this point represents the final mixing coefficients of the analysis. Otherwise, steps 350 through 364 are repeated where the corrected mixing coefficients computed in step 358 (or the new estimated mixing coefficients computed in step 362) replace the estimated mixing coefficients from the prior iteration that are used to generate the estimated spectrum for the next iteration through the steps 350 through 364. An example of a maximum number of iterations is 100. An example of a "no more negative" peaks situation is when there are no regions at least five (5) contiguous points. Five or more contiguous negative residual points may be referred to as a contiguous block. Five is an arbitrarily selected value, and may be changed based on the resolution and noise characteristics of the system on which the R4 algorithm is applied.

Many of the computations in various steps of the process 300 may be performed using techniques known in the art. For example, "peak picker" routines are known to identify peaks in a signal. In step 352, negative peaks using the criterion explained above of a certain number (e.g., five) of negative (or positive if the original measured spectrum is negative) contiguous points. To say it more generally, a peak is identified as at least a predetermined number of contiguous points that are on the opposite side, with respect to a baseline, to peaks in the measured spectrum. The "negative" nature of a point may be based on area in a negative direction, length in a negative direction and/or angle relative to peaks in the measured spectrum.

Turning to FIGS. 4, 5A, 5B, 5C, 6A, 6B, 7A, 7B, 7C, 7D, 8A, 8B, 8C, 8D, 9A, 9B, 9D, 10 and 11, with continued reference to FIG. 3, data produced at various points of the process 300 will be described to illustrate how the process 300 operates for a simulation example. FIG. 4 shows lists the names of the compounds that are members in the exemplary library. In this simulation example, the unknown substance is Carbaryl. That is, Carbaryl is not in the library spectra. A spectrum was generated by simulating a spectrum of Carbaryl, normalizing it, multiplying it by 0.5, adding it to a normalized spectrum of methanol (a member of the library spectra). The simulation was done to demonstrate the ability of the process 300 to reduce and/or reject predictions of anything except methanol.

Iteration 0

Figure 5A:
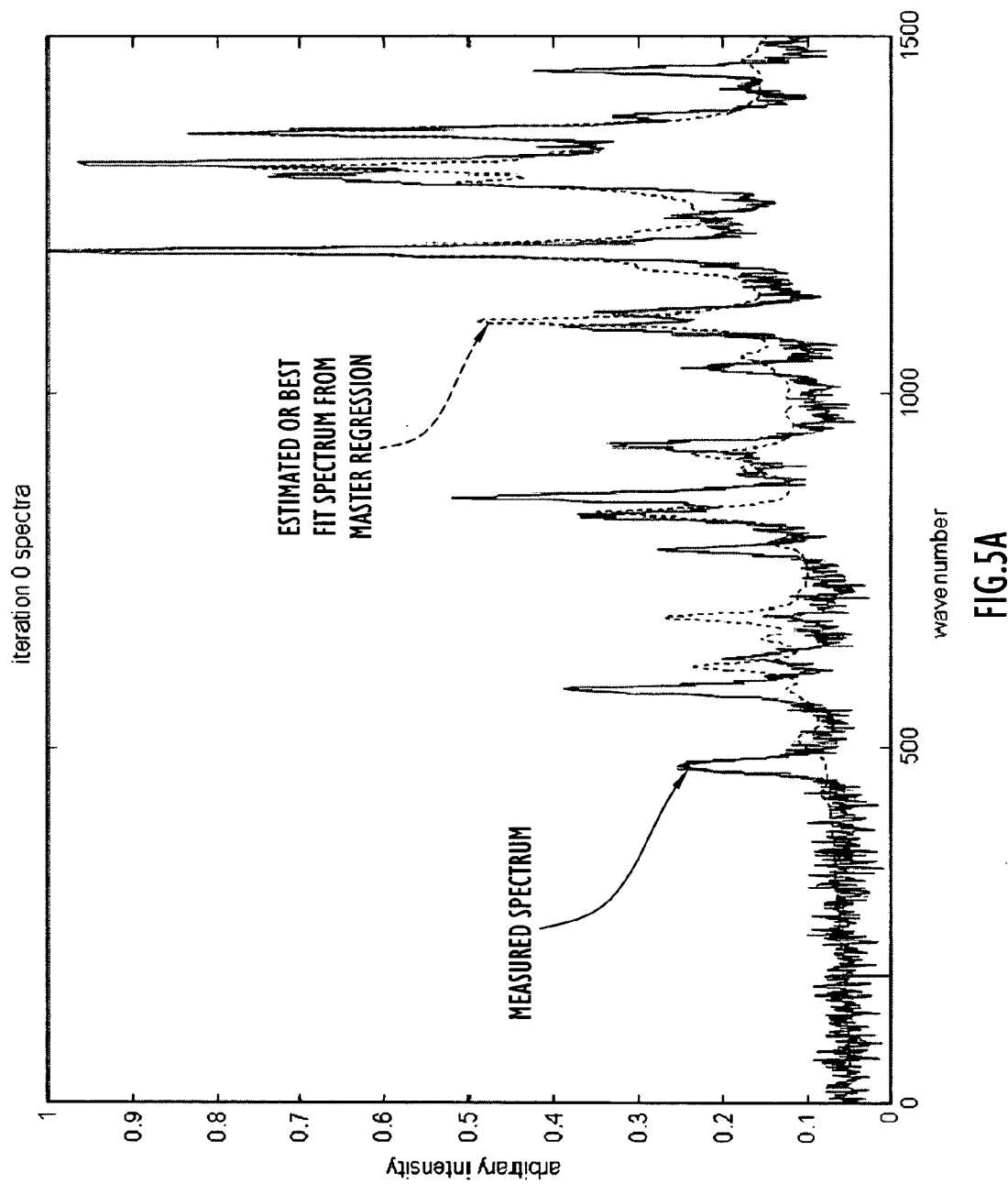
FIG. 5A is a plot showing a measured spectrum taken from a sample and the estimated or best-fit spectrum generated from the master regression coefficients.
Figure 5B:
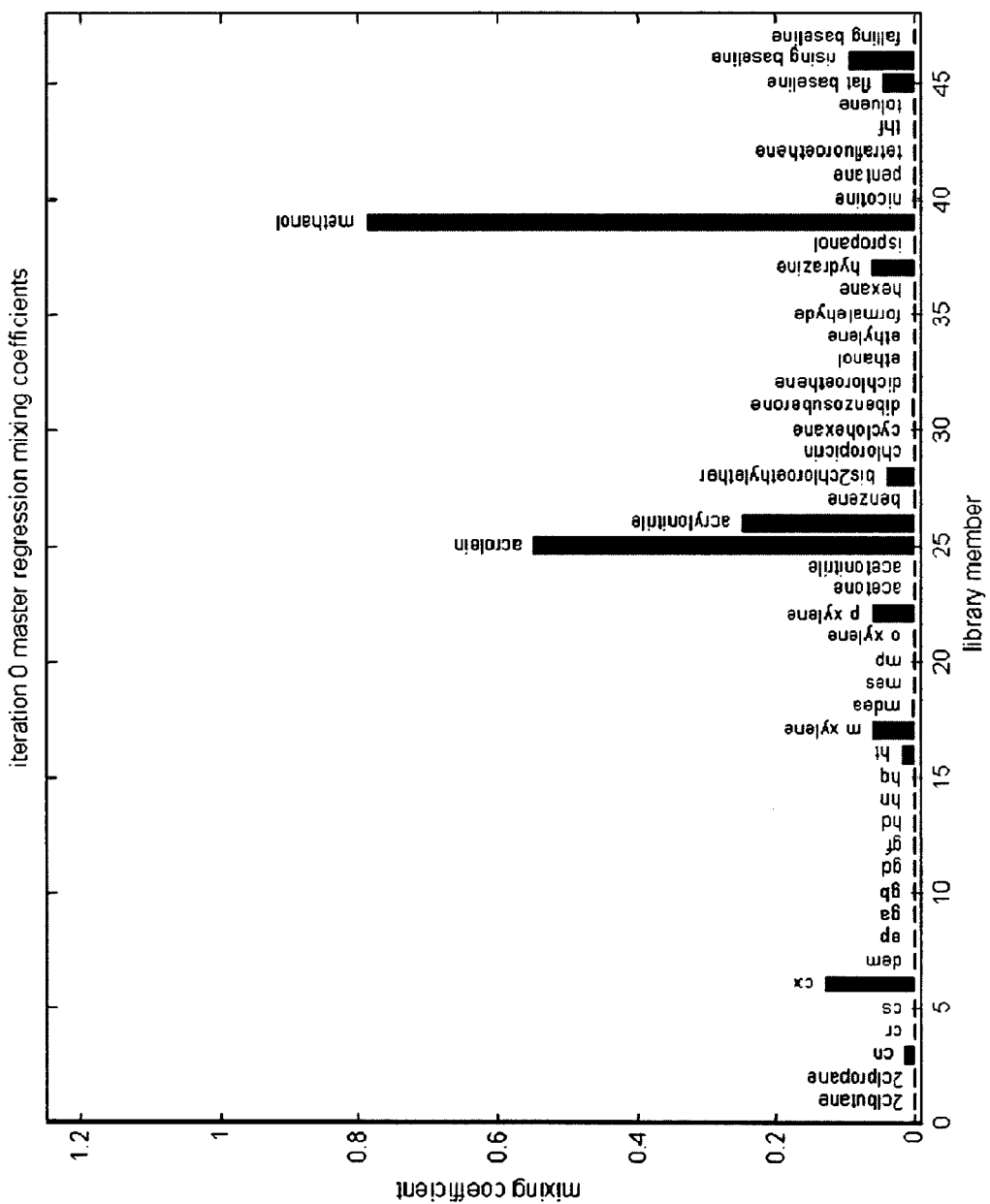
FIG. 5B is a chart showing the mixing coefficients generated from the master regression computation.
Figure 5C:
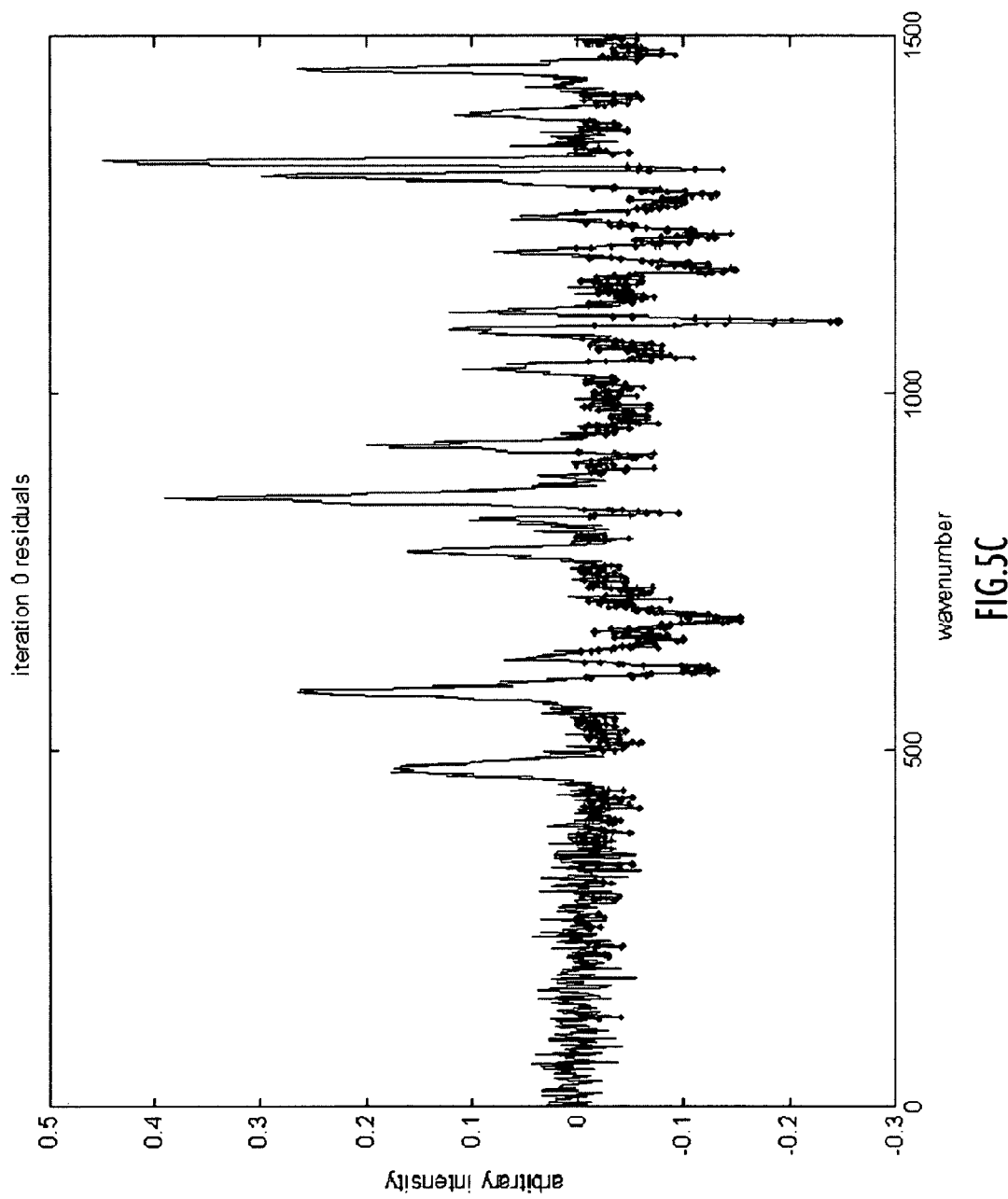
FIG. 5C is a plot showing the residual error between the measured spectrum and the best-fit estimated spectrum shown in FIG. 5A.

FIG. 5A shows the measured spectrum (dashed line) and the initial estimated or best-fit spectrum (solid line) generated from the master regression coefficients computed in step 330. FIG. 5B shows the mixing coefficients generated from the master regression computation of step 330. FIG. 5C shows the residual error between the measured spectrum and the best-fit spectrum shown in FIG. 5A.

Iteration 1

Figure 6A:
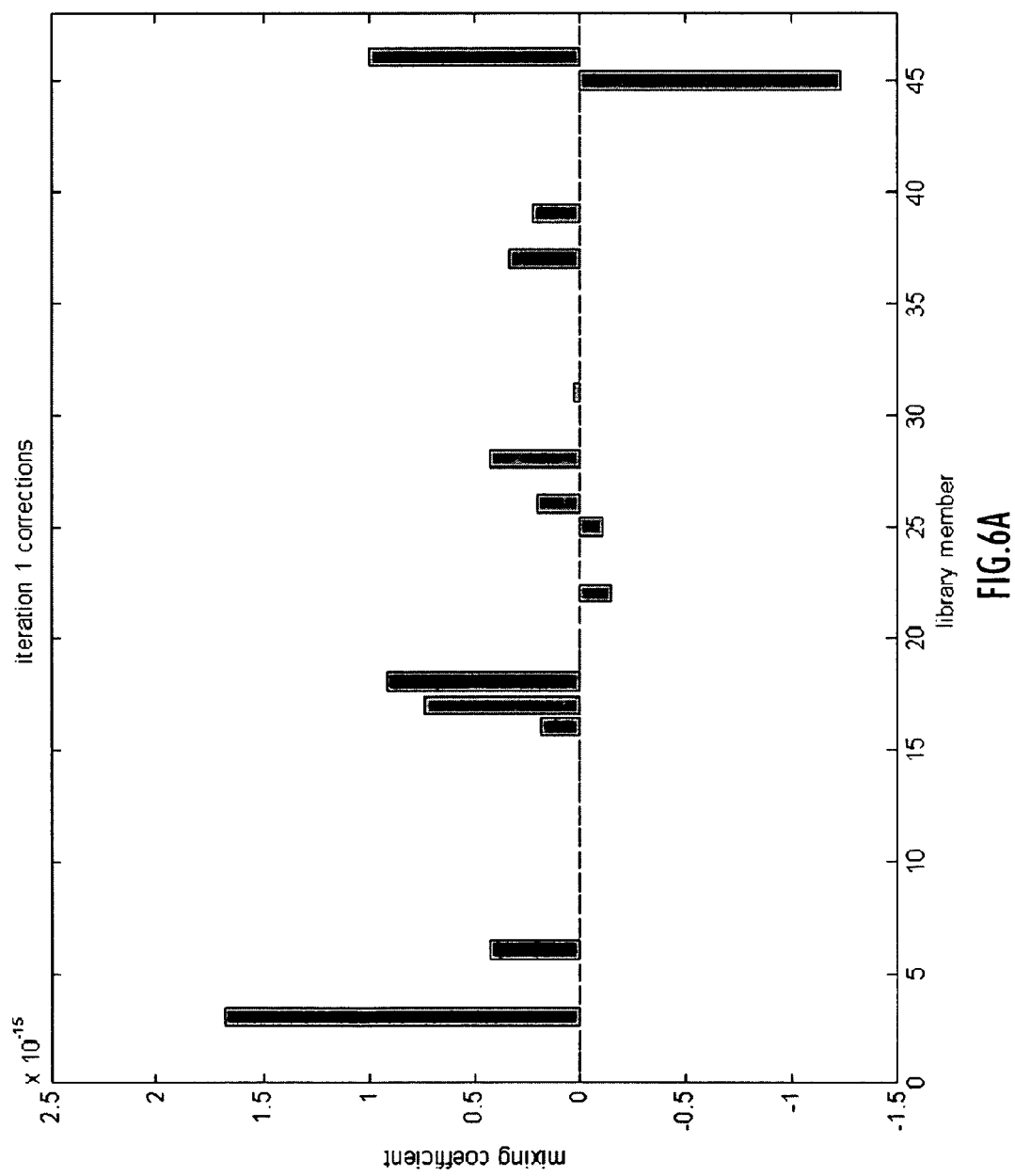
FIG. 6A is a chart showing the retro-regression coefficients computed in iteration 1 from the residuals shown in FIG. 5B.
Figure 6B:
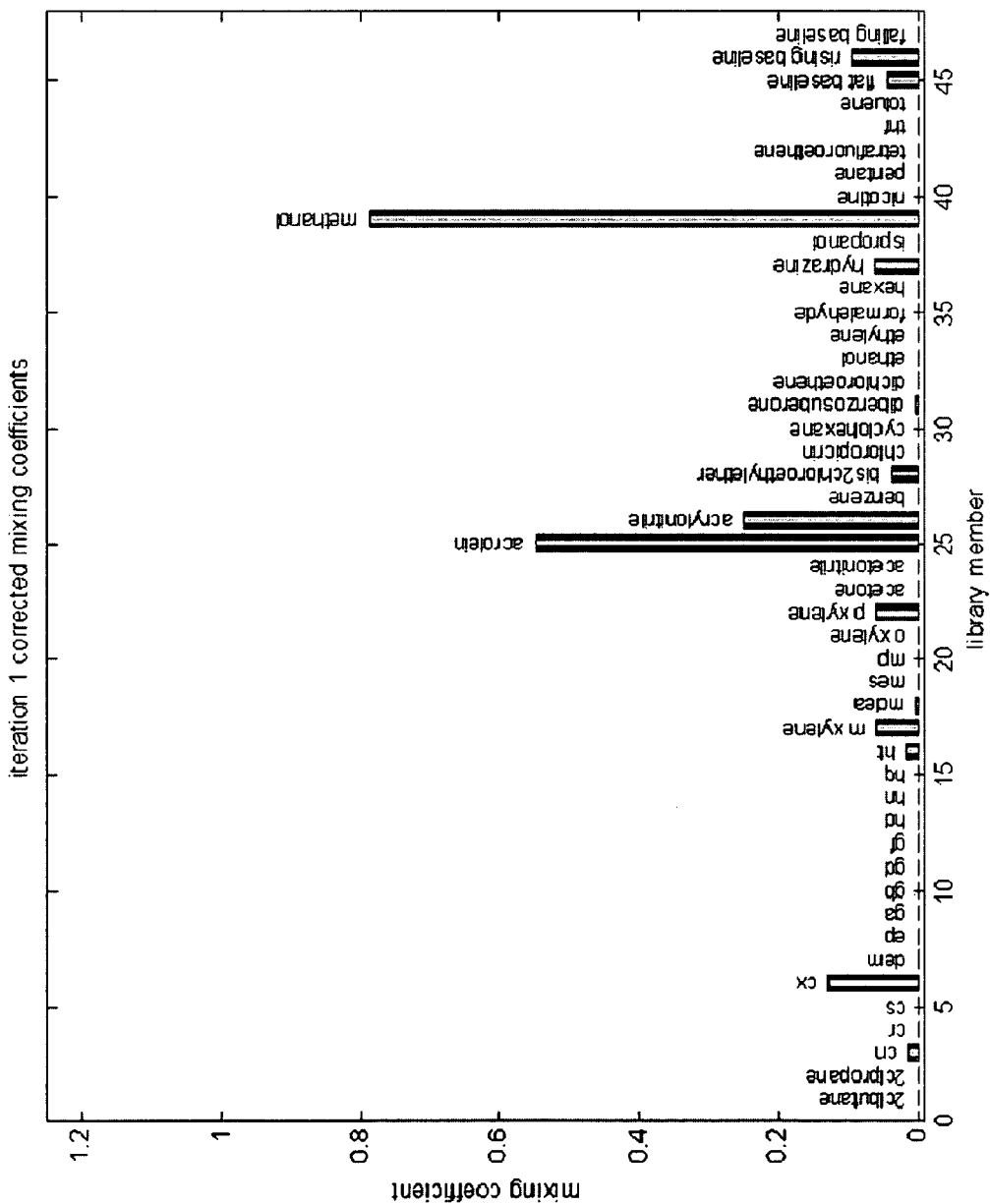
FIG. 6B is a chart showing the corrected mixing coefficients for iteration 1 computed from the retro-regression coefficients shown in FIG. 6A.

FIG. 6A shows the retro-regression coefficients computed in step 356 computed by performing a regression on the negative peaks identified in the residuals shown in FIG. 5C. FIG. 6B is a chart showing the corrected mixing coefficients computed from the retro-regression coefficients shown in FIG. 6A and from the master regression coefficients shown in FIG. 5B.

Iteration 2

Figure 7A:
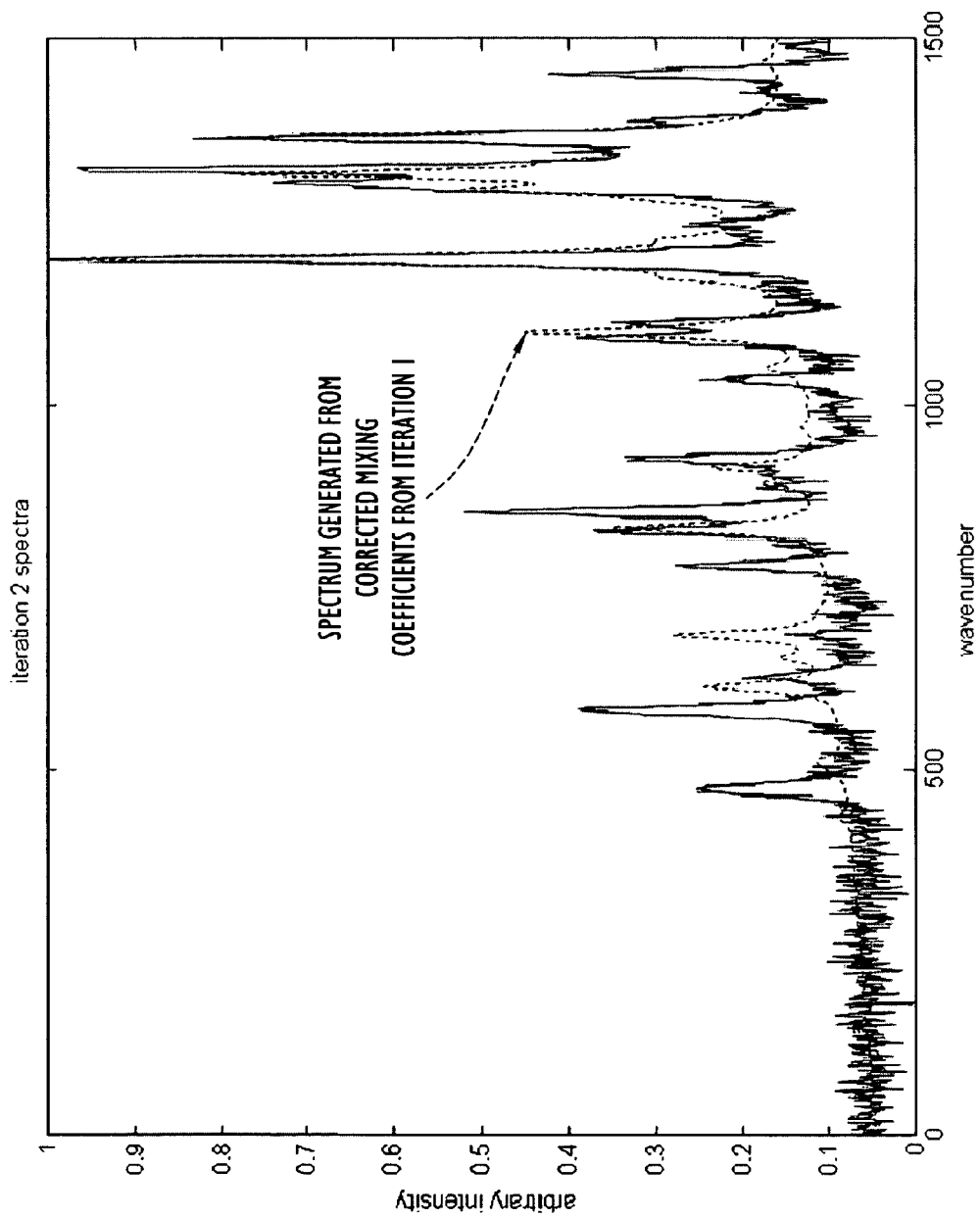
FIG. 7A is a plot showing the measured spectrum and an estimated spectrum at iteration 2 that is generated from the corrected mixing coefficients from iteration 1.
Figure 7C:
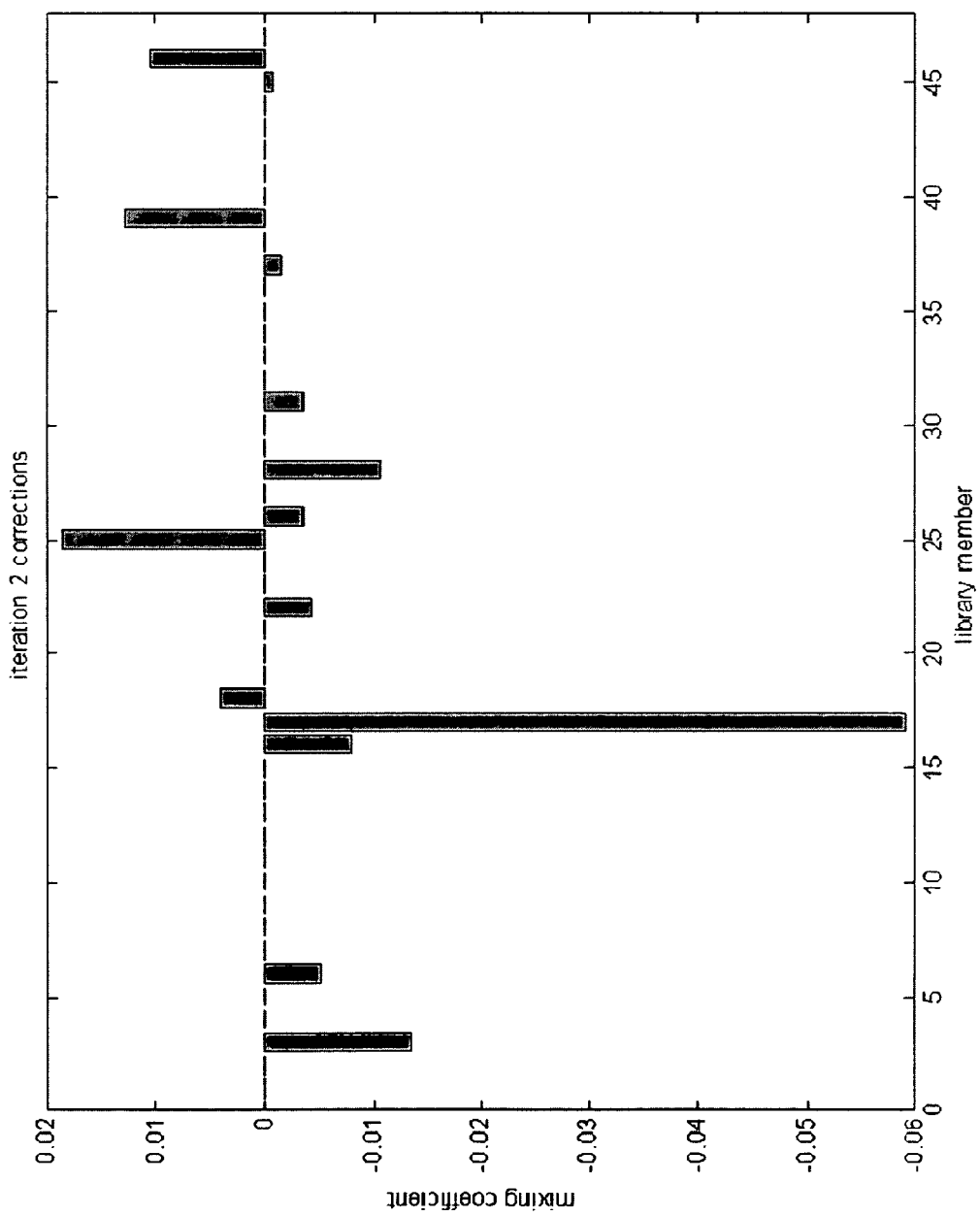
FIG. 7C is a chart showing the retro-regression coefficients computed in iteration 2 from the residuals shown in FIG. 7B.
Figure 7D:
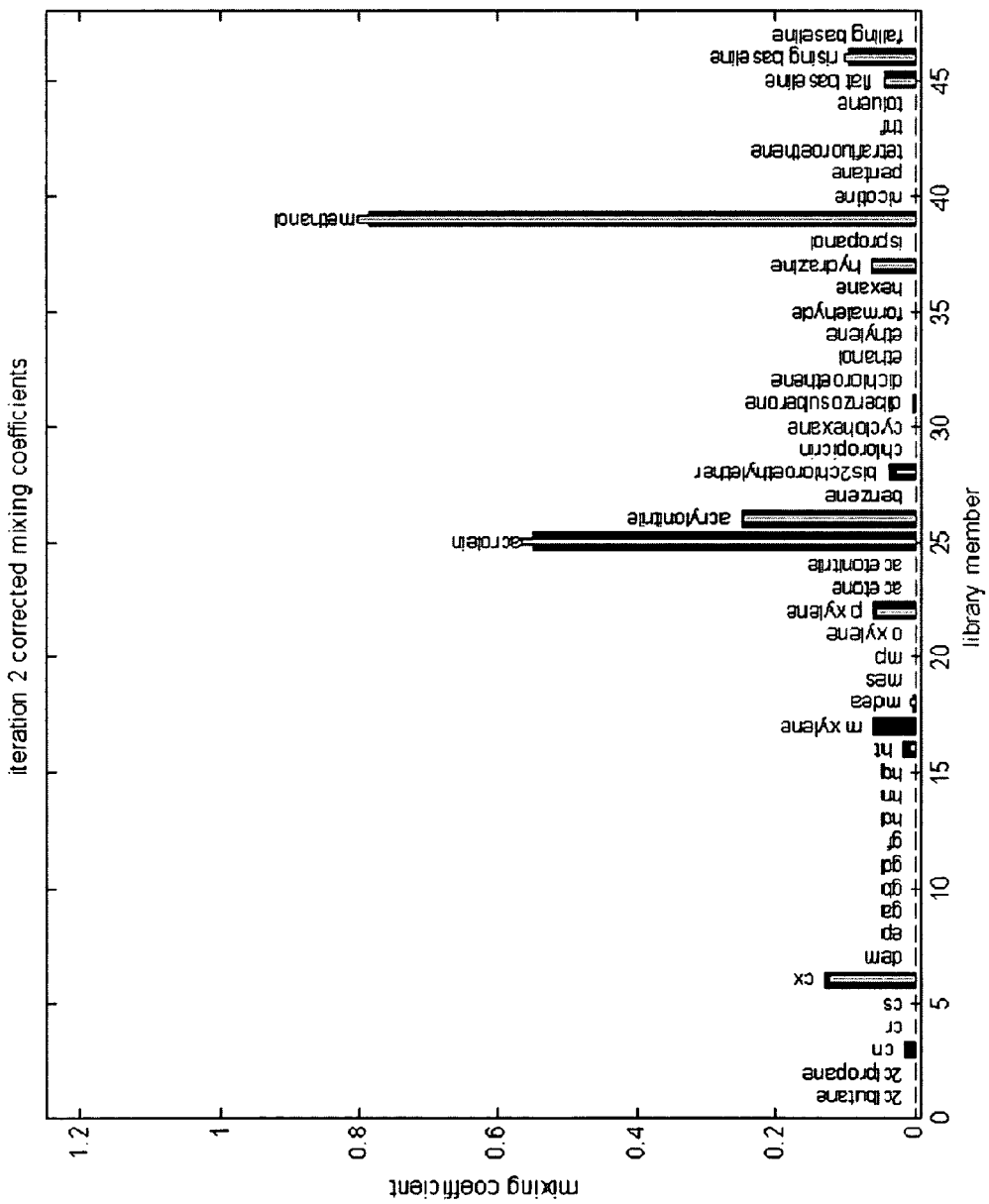
FIG. 7D is a chart showing the corrected mixing coefficients for iteration 2 computed from the retro-regression coefficients shown in FIG. 7C.

FIG. 7A is a plot showing the measured spectrum and an estimated spectrum computed from the corrected mixing coefficients shown in FIG. 6B. FIG. 7B is a plot showing the residuals computed for the estimated spectrum shown in FIG. 7A. FIG. 7C is a chart showing the retro-regression coefficients computed for the negative peaks identified in the residuals shown in FIG. 7B. FIG. 7D is a chart showing the corrected mixing coefficients computed from the retro-regression coefficients shown in FIG. 7C and the corrected mixing coefficient shown in FIG. 6B for the prior iteration.

This process repeats for several iterations as described above. At the next iteration, residuals are computed from the new mixing coefficients computed in step 362 or the corrected mixing coefficients computed in 358 from the prior iteration. Then the negative peaks are identified and isolated and a retro-regression is computed on the negative peaks. The corrected mixing coefficients are then computed by subtracting the retro-regression coefficients from the estimated mixing coefficients from the prior iteration. In this example, the process terminates after the 26th iteration for reasons explained below.

Iteration 25

Figure 8B:
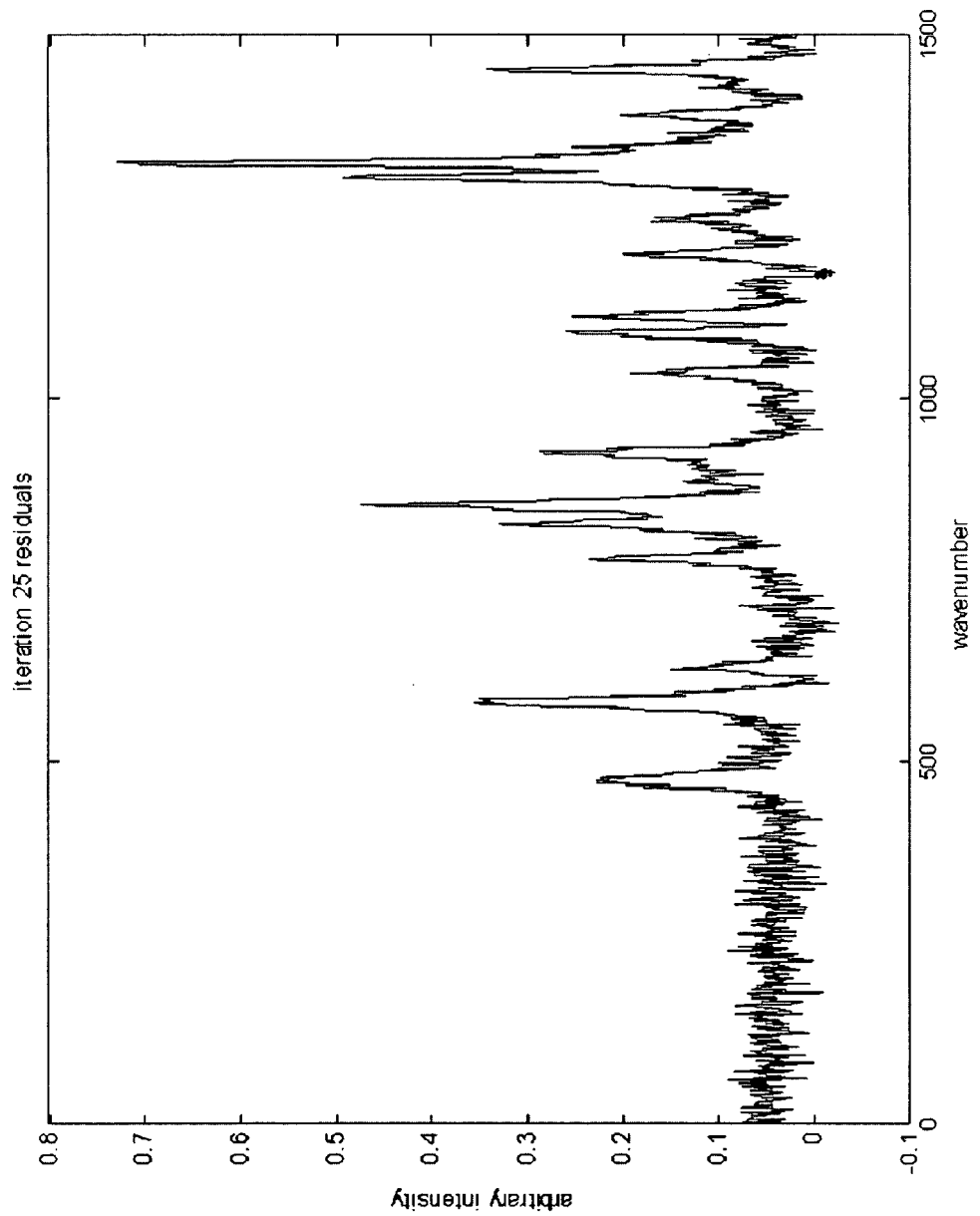
FIG. 8B is a plot showing the residual error between the measured spectrum and the estimated spectrum shown in FIG. 8A for iteration 25.
Figure 8C:
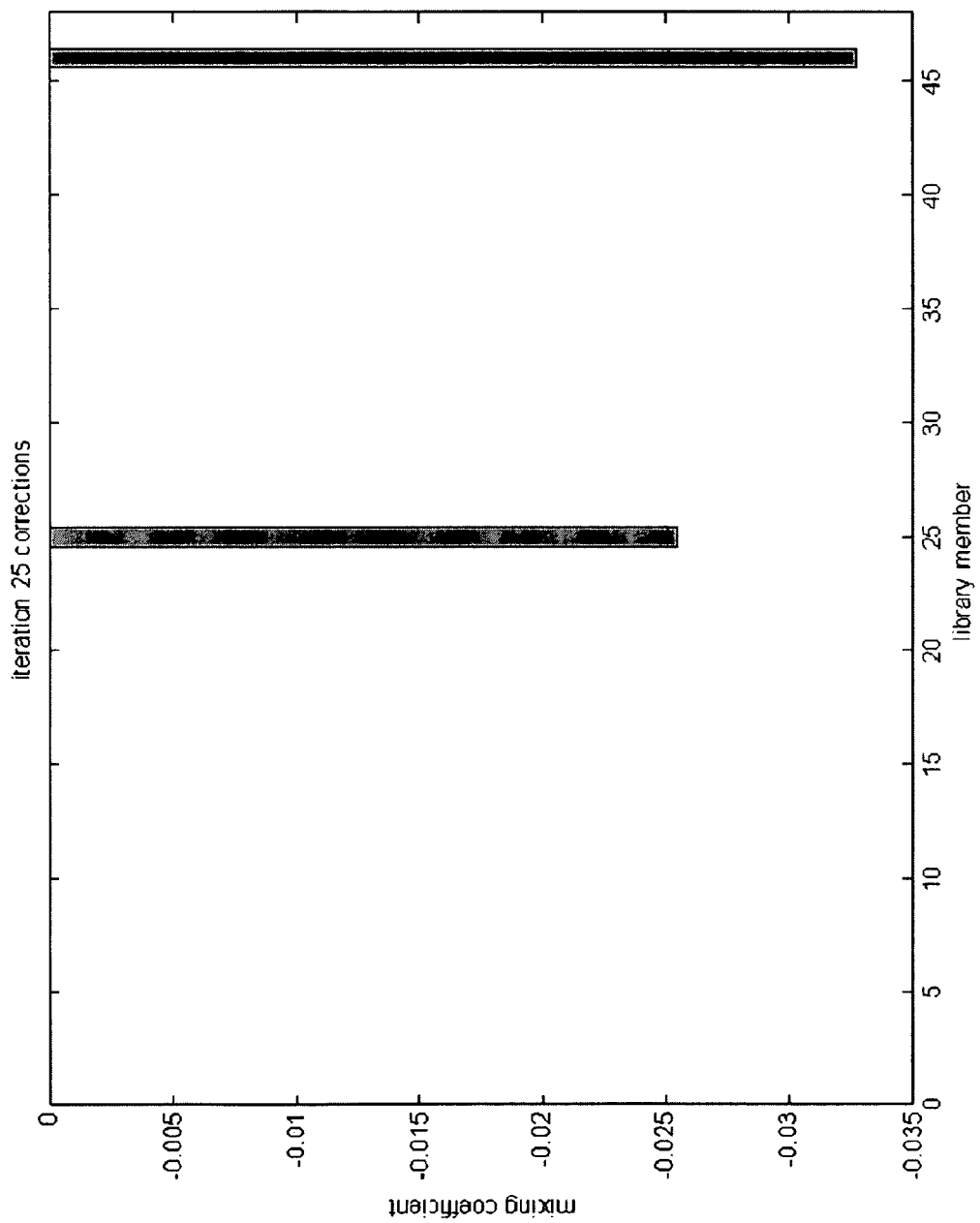
FIG. 8C is a chart showing the retro-regression coefficients computed in iteration 25 from the residuals shown in FIG. 8B.
Figure 8D:
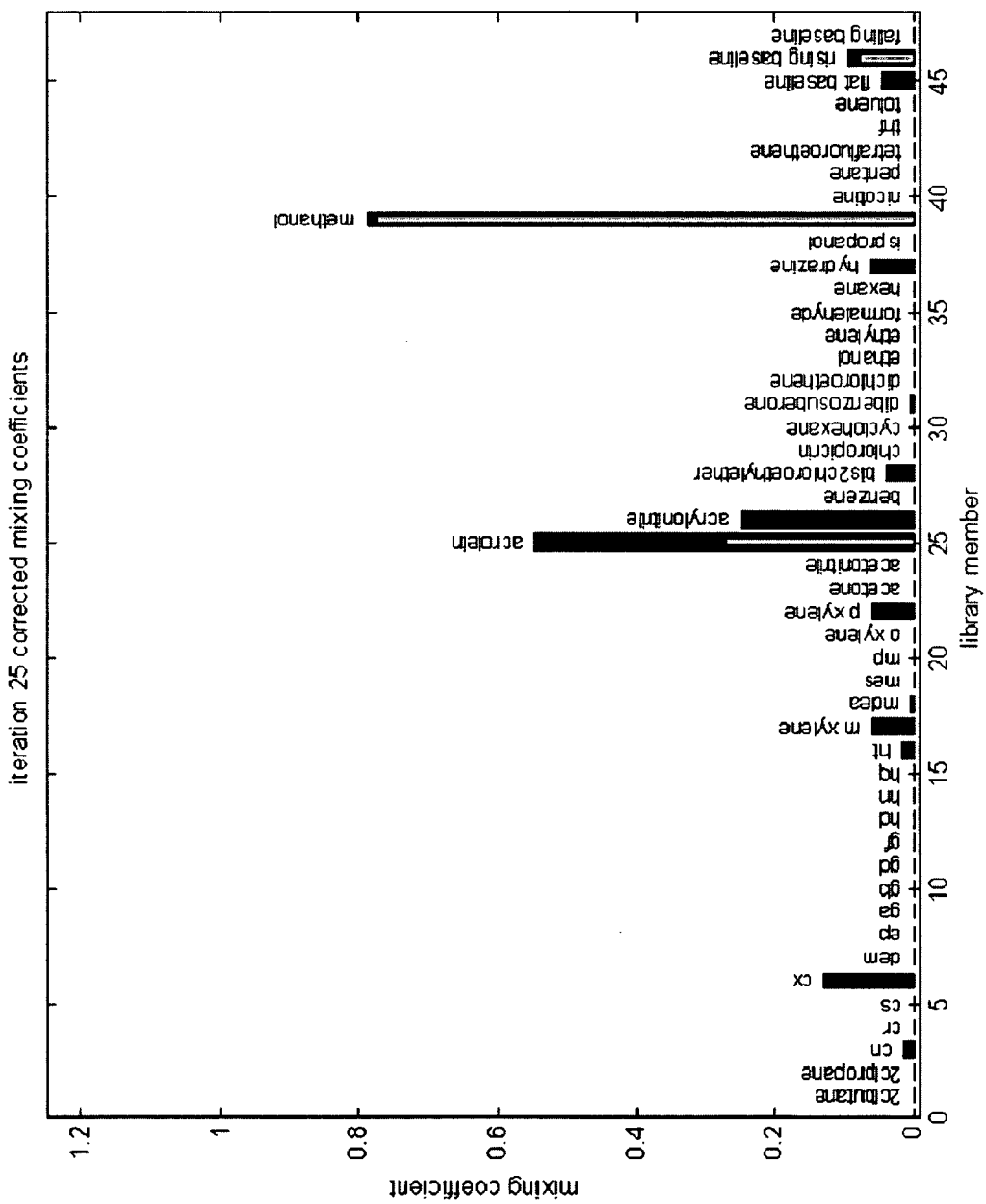
FIG. 8D is a chart showing the corrected mixing coefficients for iteration 25 computed from the retro-regression coefficients shown in FIG. 8C.

FIG. 8A shows the plots for the measured spectrum and an estimated spectrum generated from the corrected mixing coefficients computed at iteration 24 (not shown). FIG. 8B shows the residuals computed using the estimated spectrum shown in FIG. 8A. FIG. 8C shows the retro-regression coefficients computed from the one remaining negative peak of the residuals shown in FIG. 8B. FIG. 8D is a chart showing the corrected mixing coefficients computed from the retro-regression coefficients shown in FIG. 8C and the corrected mixing coefficients at iteration 24 (not shown).

Iteration 26

Figure 9A:
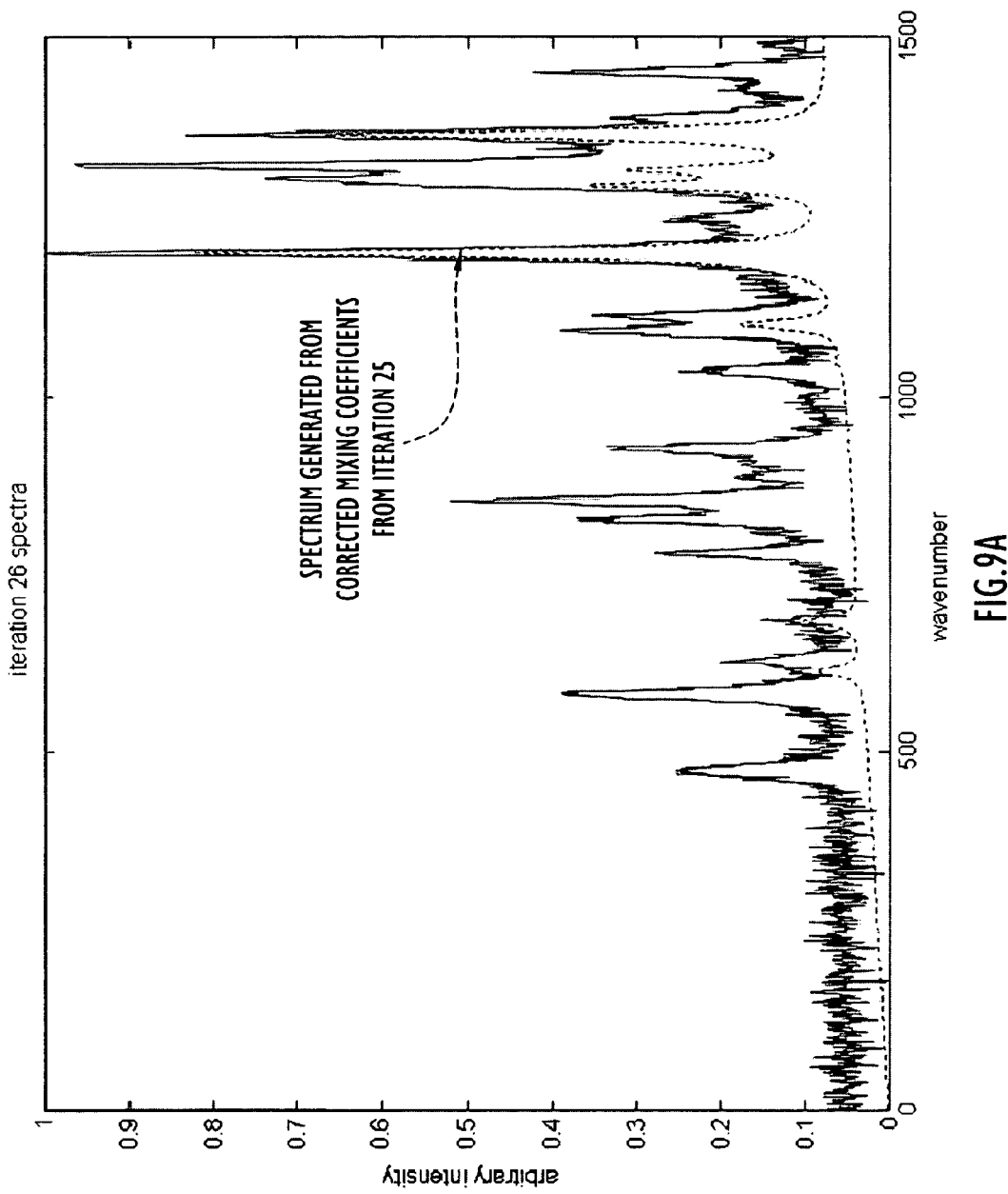
FIG. 9A is a plot showing the measured spectrum and an estimated spectrum at iteration 26 that is generated from the corrected mixing coefficients from iteration 25.
Figure 9B:
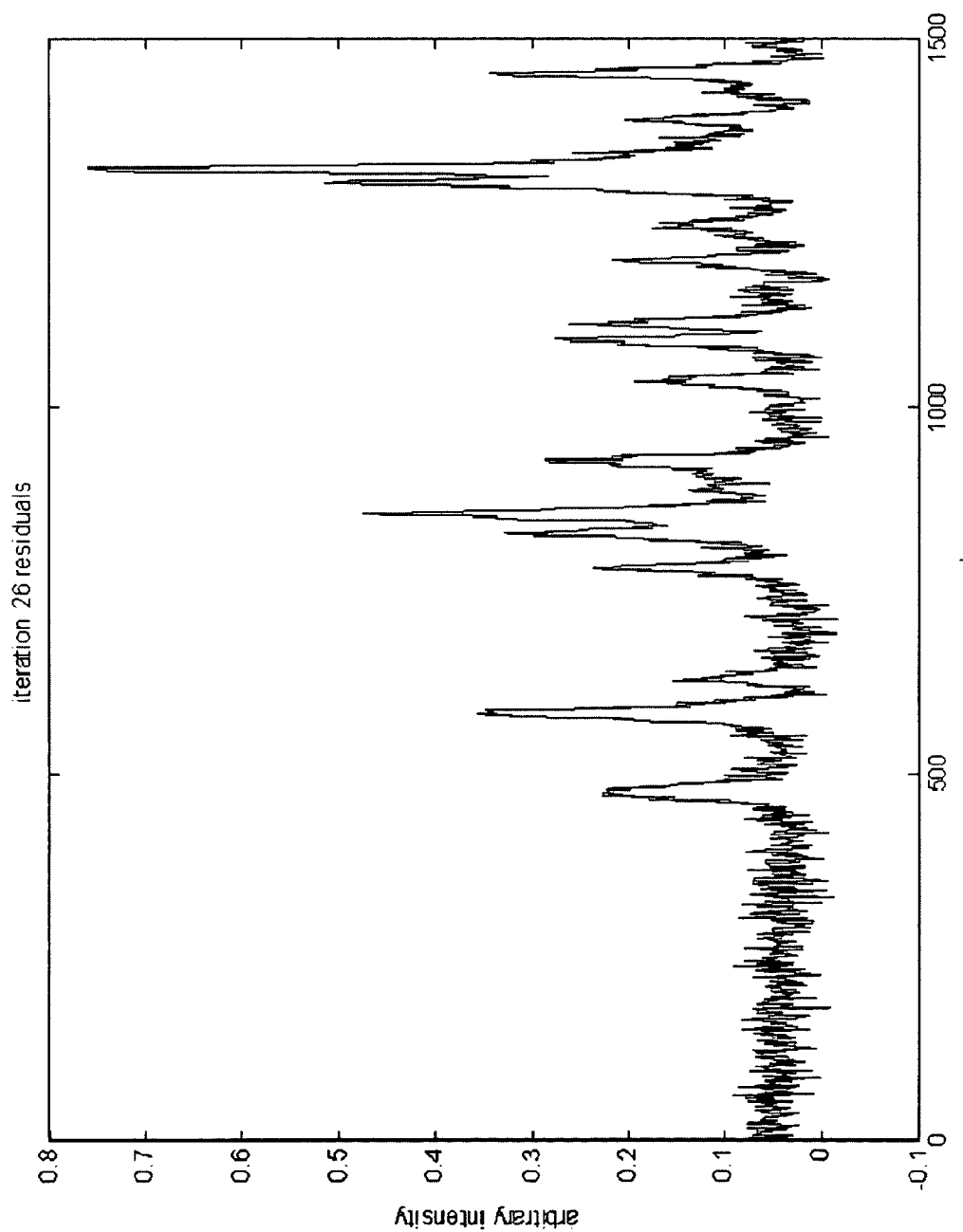
FIG. 9B is a plot showing the residual error between the measured spectrum and the estimated spectrum shown in FIG. 9A for iteration 26.
Figure 9C:
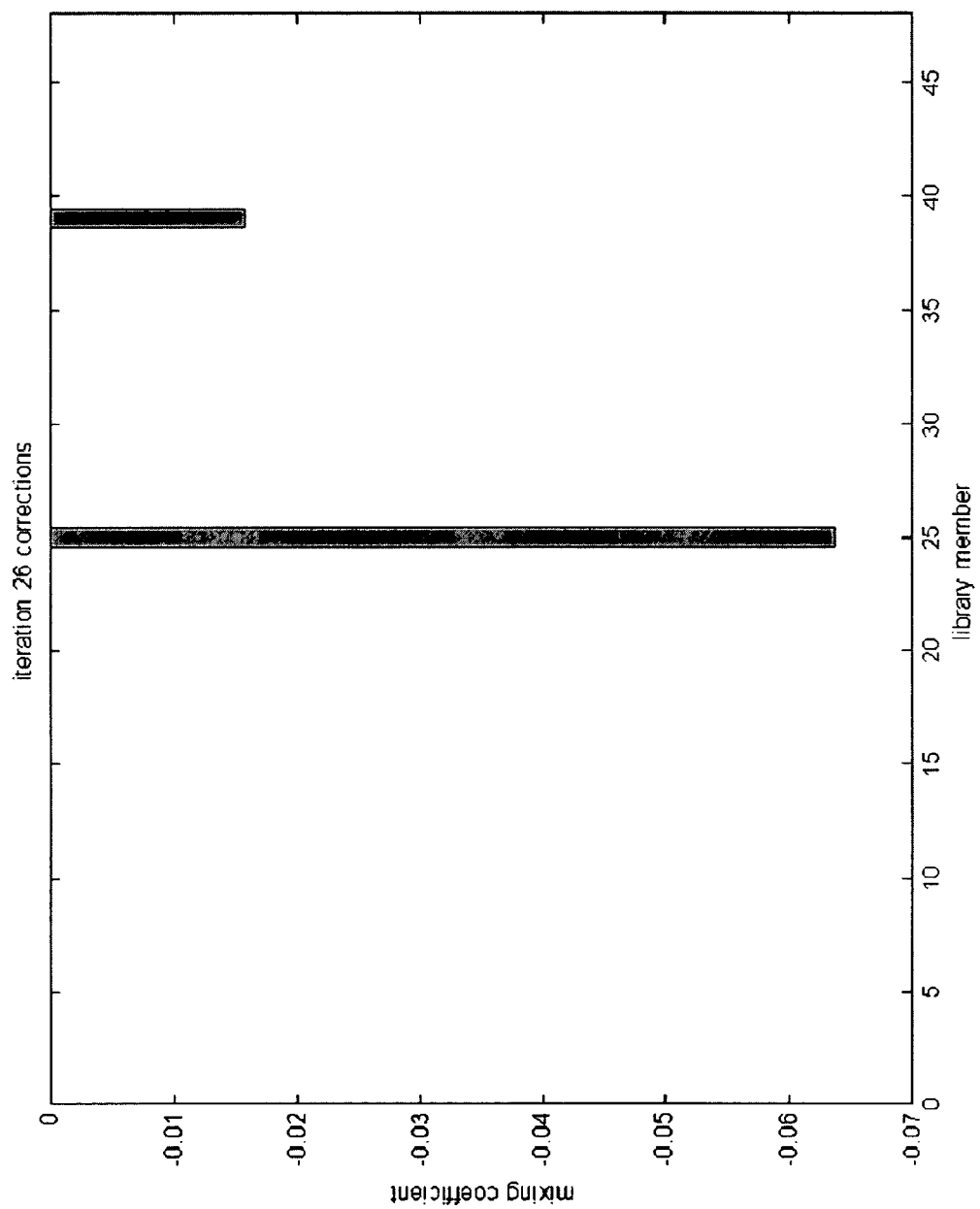
FIG. 9C is a chart showing the retro-regression coefficients computed in iteration 26 from the residuals shown in FIG. 9B.
Figure 9D:
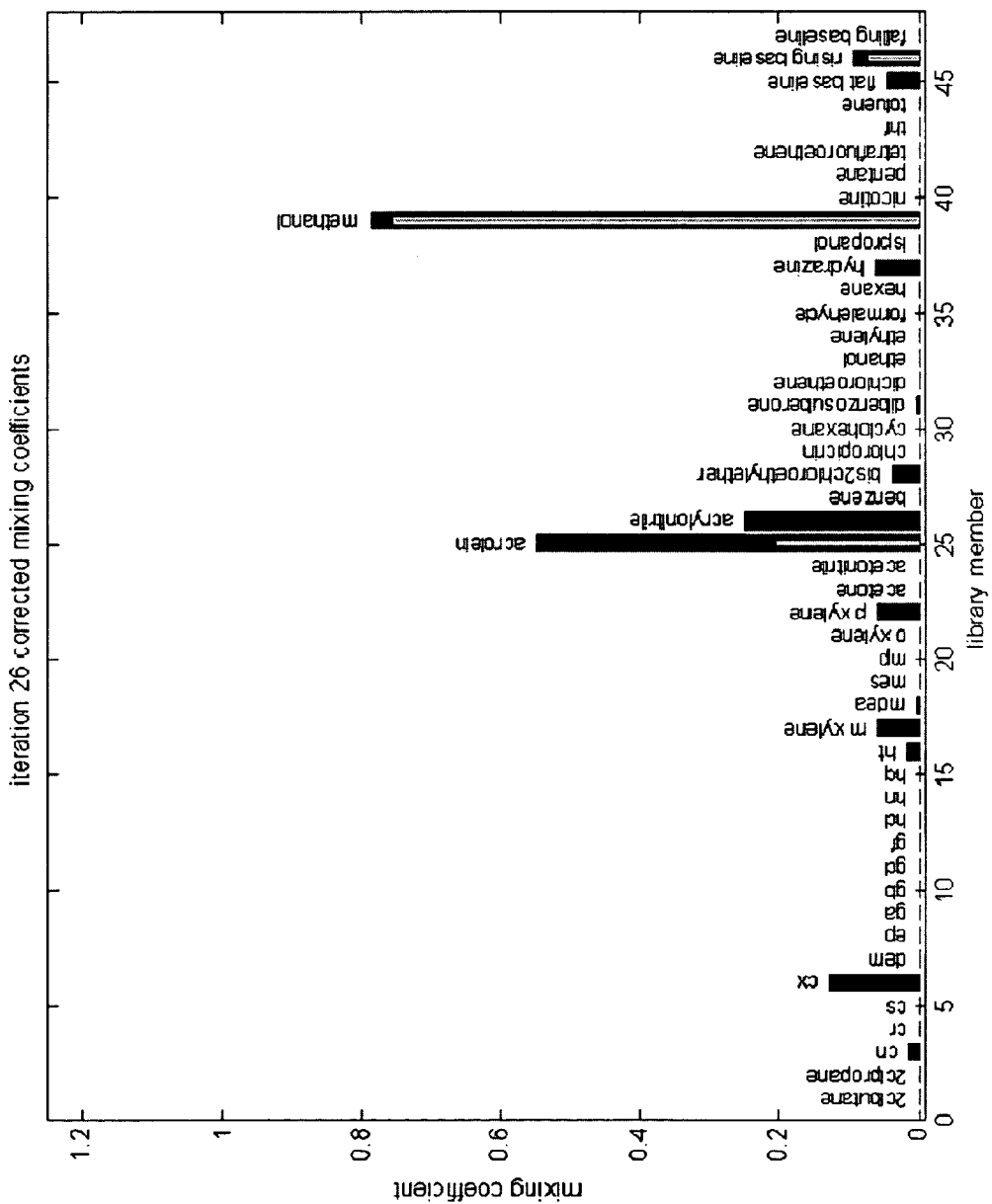
FIG. 9D is a chart showing the corrected mixing coefficients for iteration 26 computed from the retro-regression coefficients shown in FIG. 9C.

FIG. 9A shows the measured spectrum and an estimated spectrum generated from the corrected mixing coefficients shown in FIG. 8D. FIG. 9B shows the residuals computed using the estimated spectrum shown in FIG. 9A. FIG. 9C is a chart showing the retro-regression coefficients computed from the negative peaks of the residuals shown in FIG. 9D. Notice that there are no negative peaks in the residuals shown in FIG. 9C. FIG. 9D shows the corrected mixing coefficients computed from the retro-regression coefficients shown in FIG. 9C and the corrected mixing coefficients shown in FIG. 8D. Because there are no negative peaks in the residuals at the $26^{th}$ iteration, the process now terminates.

Explanation of Simulation Results

Figure 10:
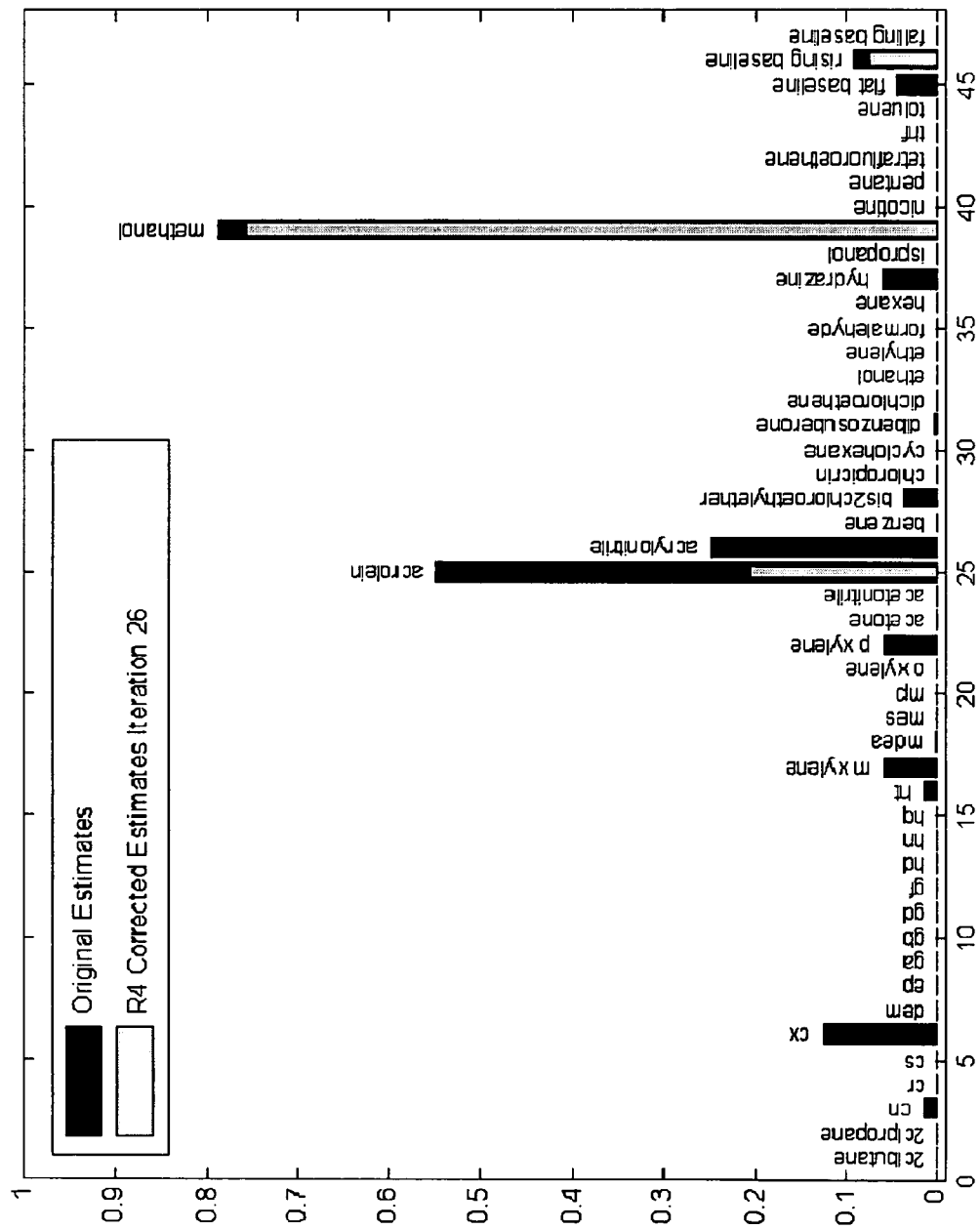
FIG. 10 is a plot showing a comparison of the corrected mixing coefficients generated using the retro-regression remediation techniques and the mixing coefficients generated without the retro-regression remediation techniques.

FIG. 10 shows the original mixing coefficients computed at the master regression step 330 and the corrected mixing coefficients at the $26^{th}$ iteration.

This figure essentially compares the performance of the R4 algorithm with a standard CLS algorithm used to analyze a mixture that has a compound that is not in the library spectra. Due to the peaks of Carbaryl, the unknown, several other chemicals, namely Acrolein, Acrylonitrile, and CX, are falsely identified as being present using a CLS algorithm, some at fairly high amounts. However, using the retro-regression remediation techniques described herein, the false positives of standard CLS are removed, and do not appear in the resulting mixing coefficients to any significant degree. Methanol appears in the corrected mixing coefficients, as it should, because it was present in the measured spectrum and is part of the library spectra. While Acrolein still appears in the corrected mixing coefficients, it is in substantially lower amounts than without the retro-regression techniques. Its amount is so low that it would not trigger a false positive identification.

The R4 algorithm removes the residuals that are due to miss-identification of library members not present in the unknown spectrum. Upon complete removal of a library member a complete recalculation of the "master" mixing coefficients is performed. This re-computation is performed because upon removal of a library member, the mixing coefficients may change. Thus, re-calculation is performed to yield a more accurate assessment of the composition of the sample. In the example data, it may be seen that performing the re-calculation upon removal of a library member does add extra computations and extends the time required to iterate, but in the end superior rejection of spurious spectra is achieved. At each re-calculation the mixings are inflated, and the R4 algorithm works to reduce them.

Figure 11:
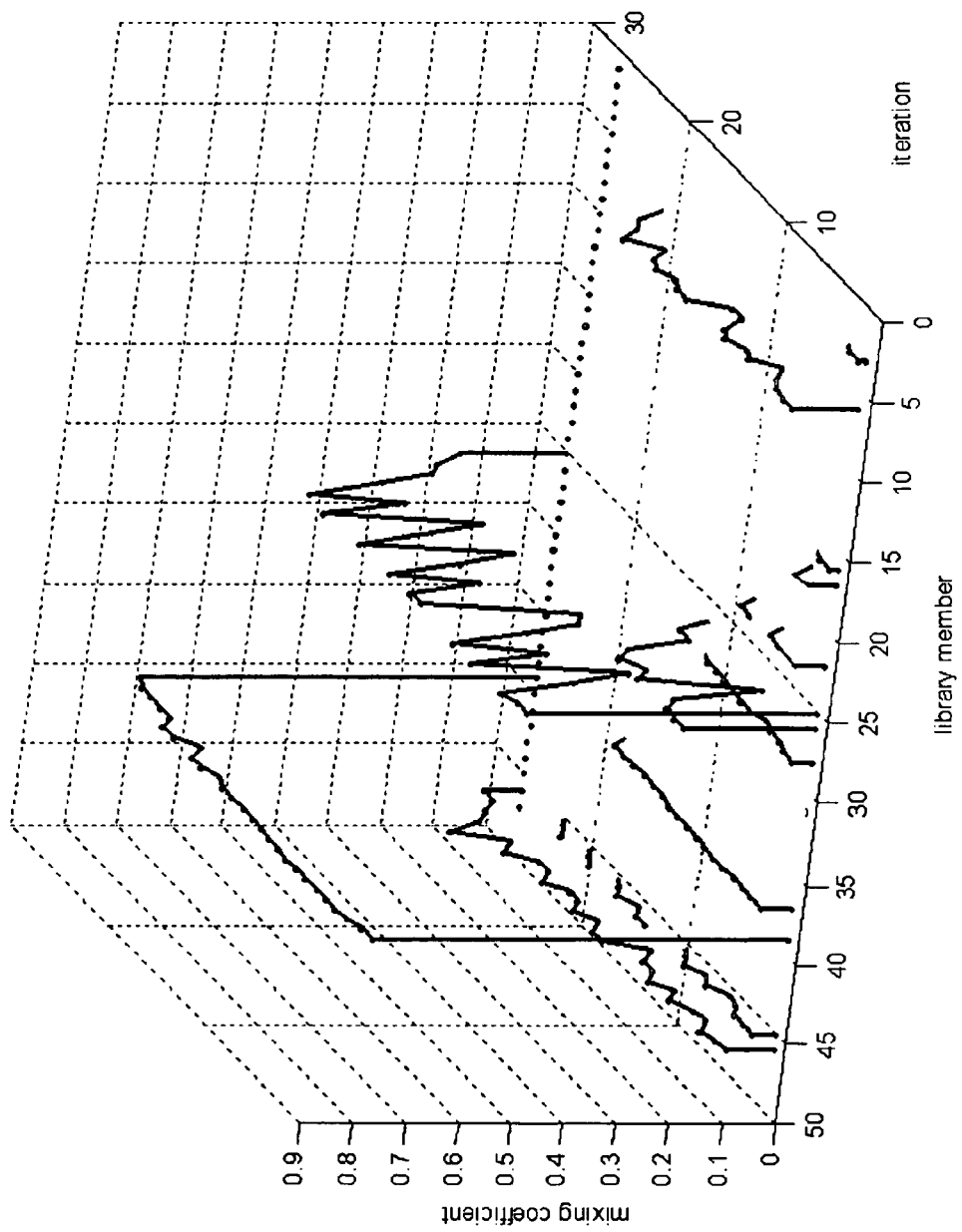
FIG. 11 is a plot showing how library members are removed from the library spectra in the retro-regression remediation process as their mixing coefficients fall below a threshold.

FIG. 11 shows that several members of the library are removed over the retro-regression iterations (step 260 in FIG. 3). Upon termination, the coefficients are strong only for the true remaining members of the library.

To summarize, a method for improving regression-based spectroscopic analysis, comprising: (a) computing a residual error between an estimated spectrum and a measured spectrum taken of a sample, wherein the estimated spectrum is derived from mixing coefficients for members of a library of spectra that are produced by computing a regression on the measured spectrum with the library; (b) identifying peaks in the residual error that extend in a direction opposite to that of peaks in the measured spectrum; (c) performing a regression on the peaks to produce retro-regression coefficients; (d) computing corrected mixing coefficients based on the retro-regression coefficients; and (e) repeating (a) through (d) with the corrected mixing coefficients computed in (d) being used to generate a new estimated spectrum for computing the residual error in (a) at the next iteration.

Similarly, a processor readable medium is provided storing instructions that, when executed by a processor, cause the processor to: (a) compute a residual error between an estimated spectrum and a measured spectrum taken of a sample, wherein the estimated spectrum is derived from a mixing coefficients for members of a library of spectra that are produced by computing a regression on the measured spectrum with the library; (b) identify peaks in the residual error that extend in a direction opposite to that of peaks in the measured spectrum; (c) perform a regression on the peaks to produce retro-regression coefficients; (d) compute corrected mixing coefficients based on the retro-regression coefficients; and repeat (a) through (d) with the corrected mixing coefficients computed in (d) being used to generate a new estimated spectrum for computing the residual error in (a) at the next iteration.

In addition, a system for spectroscopic analysis comprising: a sensor that produces data from a mixture to be analyzed, and a processor coupled to the sensor, wherein the processor is programmed to: (i) generate a measured spectrum from the data produced by the sensor; (ii) perform a regression of the measured spectrum with a library of spectra; (iii) generate estimated mixing coefficients from the regression; (iv) compute a residual error between an estimated spectrum generated from the estimated mixing coefficients and the measured spectrum; (v) identify peaks in the residual error that extend in a direction opposite to that of peaks in the measured spectrum; (vi) perform a regression on the peaks to produce retro-regression coefficients; (vii) compute corrected mixing coefficients based on the retro-regression coefficients; and (viii) repeat (iv) through (vii) with the corrected mixing coefficients computed in (vii) being used to generate a new estimated spectrum for computing the residual error in (iv) at the next iteration.

Still further, a method is provided for processing spectroscopic measured data of a sample, comprising: (a) identifying peaks in a residual error between measured data and an estimated data computed from a regression performed on the measured data, wherein the peaks extend in a direction opposite to that of peaks in the measured data; (b) performing a regression on the peaks; (c) computing a corrected data based on the regression of the peaks; (d) computing a new residual error between the measured data and the corrected data; and (e) repeating (a) through (d) using the new residual error.

The system and methods described herein may be embodied in other specific forms without departing from the spirit or essential characteristics thereof. The foregoing embodiments are therefore to be considered in all respects illustrative and not meant to be limiting.

What is claimed is:

1. A method for improving regression-based spectroscopic analysis, comprising:
   a. computing a residual error between an estimated spectrum and a measured spectrum taken of a sample of a solid, liquid or gas substance to be analyzed using spectroscopy techniques, wherein the estimated spectrum is derived from mixing coefficients for members of a library spectra that are produced by computing a regression on the measured spectrum with the library spectra;
   b. identifying peaks in the residual error that extend in a direction opposite to that of peaks in the measured spectrum;
   c. performing a regression on the peaks in the residual error that extend in a direction opposite to that of the peaks in the measured spectrum to produce retro-regression coefficients;
   d. computing corrected mixing coefficients based on the retro-regression coefficients by subtracting the retro-regression coefficients from the mixing coefficients for the estimated spectrum for a current iteration;
   e. repeating (a) through (d) with the corrected mixing coefficients computed in (d) being used to generate a new estimated spectrum for computing the residual error in (a) at the next iteration; and
   f. determining whether a chemical or biological constituent whose spectra is contained in said library spectra is present in said sample based on said new estimated spectrum.

2. The method of claim 1, and further comprising (d)(1) removing a member of the library spectra whose mixing coefficient in the corrected mixing coefficients is less than a threshold.

3. The method of claim 2, wherein when a member of the library spectra is removed, further comprising (d)(2) performing a regression of the measured spectrum with the library spectra without the member that was removed to produce new mixing coefficients, and wherein (e) repeating comprises repeating (a) computing, (b) identifying, (c) performing, (d) computing, (d)(1) removing and (d)(2) performing, wherein the new mixing coefficients being used to generate a new estimated spectrum for computing the residual error at the next iteration.

4. The method of claim 3, wherein (e) repeating comprises repeating (a) through (d)(2) until no members of the library spectra remain.

5. The method of claim 1, wherein (e) repeating comprises repeating (a) through (d) until there are no more peaks in the residual error.

6. The method of claim 1, wherein (b) identifying comprises identifying a peak as at least a predetermined number of contiguous points that are on the opposite side, with respect to a baseline, to peaks in the measured spectrum.

7. The method of claim 6, wherein (e) repeating comprises repeating (a) through (d) until there are no more regions in the residual error having at least the predetermined number of contiguous points.

8. A processor readable medium storing instructions that, when executed by a processor, cause the processor to:
   a. compute a residual error between an estimated spectrum and a measured spectrum taken of a sample of a solid, liquid or gas substance to be analyzed using spectroscopy techniques, wherein the estimated spectrum is derived from a mixing coefficients for members of a library spectra that are produced by computing a regression on the measured spectrum with the library spectra;
   b. identify peaks in the residual error that extend in a direction opposite to that of peaks in the measured spectrum;
   c. perform a regression on the peaks in the residual error that extend in a direction opposite to that of the peaks in the measured spectrum to produce retro-regression coefficients;
   d. compute corrected mixing coefficients based on the retro-regression coefficients by subtracting the retro-regression coefficients from the mixing coefficients for the estimated spectrum for a current iteration;
   e. repeat (a) through (d) with the corrected mixing coefficients computed in (d) being used to generate a new estimated spectrum for computing the residual error in (a) at the next iteration; and
   f. determine whether a chemical or biological constituent whose spectra is contained in said library spectra is present in said sample based on said new estimated spectrum.

9. The processor readable medium of claim 8, and further comprising instructions stored on the medium that, when executed, cause the processor to (d)(1) remove a member of the library spectra whose mixing coefficient in the corrected mixing coefficients is less than a threshold.

10. The processor readable medium of claim 9, and further comprising instructions stored on the medium that, when executed, cause the processor to (d)(2) perform a regression of the measured spectrum with the library spectra without the member that was removed to produce new mixing coefficients, and that cause the processor to (e) repeat (a) through (d)(2) with the new mixing coefficients being used to generate a new estimated spectrum for computing the residual error at the next iteration.

11. The processor readable medium of claim 10, and further comprising instructions stored on the medium that, when executed, cause the processor to repeat (a) through (d)(2) until no members of the library spectra remain.

12. The processor readable medium of claim 8, and further comprising instructions stored on the medium that, when executed, cause the processor to repeat (a) through (d) until there are no more peaks in the residual error.

13. The processor readable medium of claim 8, and further comprising instructions stored on the medium that, when executed, cause the processor to identify a peak as at least a predetermined number of contiguous points that are on the opposite side, with respect to a baseline, to peaks in the measured spectrum.

14. The processor readable medium of claim 8, and further comprising instructions stored on the medium that, when executed, cause the processor to repeat (a) through (d) until there are no more regions in the residual error having at least the predetermined number of contiguous points.

15. A system for spectroscopic analysis comprising:
   a. a sensor that produces data from a sample of a solid, liquid or gas substance to be analyzed using spectroscopy techniques; and b. a processor coupled to the sensor, wherein the processor is programmed to:
  i. generate a measured spectrum from the data produced by the sensor;
  ii. perform a regression of the measured spectrum with a library spectra;
  iii. generate estimated mixing coefficients from the regression;
  iv. compute a residual error between an estimated spectrum generated from the estimated mixing coefficients and the measured spectrum;
  v. identify peaks in the residual error that extend in a direction opposite to that of peaks in the measured spectrum;
  vi. perform a regression on the peaks in the residual error that extend in a direction opposite to that of the peaks in the measured spectrum to produce retro-regression coefficients;
  vii. compute corrected mixing coefficients based on the retro-regression coefficients by subtracting the retro-regression coefficients from the mixing coefficients for the estimated spectrum for a current iteration;
  viii. repeat (iv) through (vii) with the corrected mixing coefficients computed in (vii) being used to generate a new estimated spectrum for computing the residual error in (iv) at the next iteration; and
  ix. determine whether a chemical or biological constituent whose spectra is contained in said library spectra is present in said sample based on said new estimated spectrum.

16. The system of claim 15, wherein the processor is programmed to remove a member of the library spectra whose mixing coefficient in the corrected mixing coefficients is less than a threshold.

17. The system of claim 16, wherein the processor is programmed to perform a regression of the measured spectrum with the library spectra without the member that was removed to produce new mixing coefficients, and repeating (iv) through (vii) with the new mixing coefficients being used to generate a new estimated spectrum for computing the residual error at the next iteration.

* * * * *